(12) United States Patent
Herrmann et al.

(10) Patent No.: US 7,456,133 B2
(45) Date of Patent: Nov. 25, 2008

(54) SUBSTITUTED ARYLKETONES

(75) Inventors: Stefan Herrmann, Langenfeld (DE);
Dorothee Hoischen, Dusseldorf (DE);
Kristian Kather, Lagenfeld (DE);
Klaus-Helmut Muller, Dusseldorf (DE);
Otto Schallner, Monheim (DE);
Hans-Georg Schwarz, Lagenfeld (DE);
Mark Wilhelm Drewes, Langenfeld (DE); Peter Dahmen, Neuss (DE);
Dieter Feucht, Monheim (DE); Rolf Pontzen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 11/483,892

(22) Filed: Jul. 10, 2006

(65) Prior Publication Data
US 2006/0252647 A1 Nov. 9, 2006

Related U.S. Application Data

(62) Division of application No. 10/477,031, filed as application No. PCT/EP02/04701 on Apr. 29, 2002, now Pat. No. 7,112,554.

(30) Foreign Application Priority Data
May 9, 2001 (DE) ................................. 101 22 445
Jul. 26, 2001 (DE) ................................. 101 36 449

(51) Int. Cl.
*A01N 43/80* (2006.01)
*A01N 43/56* (2006.01)
*C07D 261/08* (2006.01)
*C07D 231/20* (2006.01)

(52) U.S. Cl. ....................... 504/271; 504/280; 548/248; 548/369.4

(58) Field of Classification Search ................. 504/280; 548/369.4
See application file for complete search history.

(56) References Cited

U.S. PATENT DOCUMENTS

| | | | |
|---|---|---|---|
| 4,780,127 A | 10/1988 | Michaely et al. ............... 71/103 |
| 4,806,146 A | 2/1989 | Carter ........................... 71/98 |
| 4,816,066 A | 3/1989 | Michaely et al. ............... 71/123 |
| 4,946,981 A | 8/1990 | Carter et al. ................. 558/415 |
| 4,986,845 A | 1/1991 | Oya et al. ....................... 71/92 |
| 5,006,158 A | 4/1991 | Carter et al. .................... 71/98 |
| 5,085,688 A | 2/1992 | Michaely et al. ............... 71/103 |
| 5,110,343 A | 5/1992 | Ueda et al. ...................... 71/88 |
| RE34,779 E | 11/1994 | Oya et al. .................... 504/282 |
| 5,371,063 A | 12/1994 | Cramp et al. ................ 504/270 |
| 5,374,606 A | 12/1994 | Cramp et al. ................ 504/270 |
| 5,489,570 A | 2/1996 | Geach et al. ................. 504/261 |
| 5,650,533 A | 7/1997 | Roberts et al. ................ 560/17 |
| 5,656,573 A | 8/1997 | Roberts et al. ............... 504/271 |
| 5,747,424 A | 5/1998 | Roberts et al. ............... 504/271 |
| 5,804,532 A | 9/1998 | Cain et al. ................... 504/309 |
| 5,834,402 A | 11/1998 | Von Deyn et al. ........... 504/271 |
| 5,846,906 A | 12/1998 | von Deyn et al. ........... 504/221 |
| 5,846,907 A | 12/1998 | von Deyn et al. ........... 504/221 |
| 5,849,928 A | 12/1998 | Hawkins ..................... 548/248 |
| 5,859,283 A | 1/1999 | Cramp ....................... 560/124 |
| 5,863,865 A | 1/1999 | Lee et al. .................... 504/271 |
| 5,948,917 A | 9/1999 | Adachi et al. ............... 548/247 |
| 6,004,903 A | 12/1999 | von Deyn et al. ........... 504/239 |
| 6,124,469 A | 9/2000 | Rheinheimer et al. ....... 548/240 |
| 6,150,583 A | 11/2000 | Prusiner et al. ................ 800/4 |
| 6,153,759 A | 11/2000 | von Deyn et al. ........... 548/131 |
| 6,156,702 A | 12/2000 | Engel et al. ................. 504/282 |
| 6,165,944 A | 12/2000 | von Deyn et al. ........... 504/271 |
| 6,207,618 B1 * | 3/2001 | Engel et al. ................. 504/282 |
| 6,297,198 B1 | 10/2001 | Lee ............................. 504/271 |
| 6,432,881 B1 | 8/2002 | Engel et al. ................. 504/280 |
| 6,559,100 B1 | 5/2003 | Engel et al. ................. 504/223 |
| 2002/0025910 A1 | 2/2002 | Deyn et al. .................. 504/263 |

FOREIGN PATENT DOCUMENTS

| | | |
|---|---|---|
| CA | 1314557 | 3/1993 |
| CA | 2190001 | 11/1995 |
| CA | 2338304 | 2/2000 |
| CA | 2 252 543 | 1/2003 |
| CA | 2 075 348 | 10/2003 |
| WO | 97/27187 | 7/1997 |
| WO | 97/46530 | 12/1997 |
| WO | 98/28981 | 7/1998 |
| WO | 99/03856 | 1/1999 |
| WO | 99/62520 | 12/1999 |
| WO | 00/21924 | 4/2000 |
| WO | 00/68227 | 11/2000 |
| WO | 01/23367 | 4/2001 |

* cited by examiner

*Primary Examiner*—Rei-tsang Shiao
*Assistant Examiner*—Joseph R Kosack
(74) *Attorney, Agent, or Firm*—Raymond J. Harmuth; Richard E. L. Henderson

(57) ABSTRACT

The invention relates to novel aryl ketones of the formula (I)

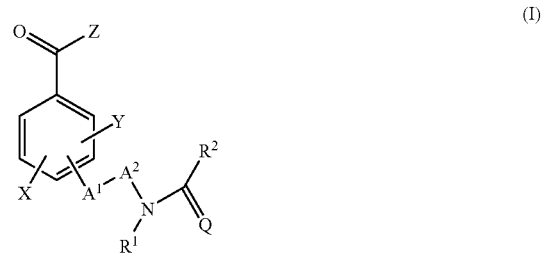

in which
$A^1, A^2, Q, R^1, R^2, X, Y$ and $Z$ are as defined in the description, their use as herbicides and processes and intermediates for their preparation.

8 Claims, No Drawings

SUBSTITUTED ARYLKETONES

This application is a divisional patent application of application Ser. No. 10/477,031, filed Apr. 15, 2004, now U.S. Pat. No. 7,112,554, which issued Sep. 26, 2006, which was the national stage of PCT/EP02/04701 filed Apr. 29, 2002, which in turn claimed priority of German Patent Application No. 101 22 445 filed May 9, 2001 and German Patent Application No. 101 35 449 filed Jul. 26, 2001.

The present invention relates to novel substituted aryl ketones, to a process for their preparation and to their use as plant treatment agents, in particular as herbicides.

It is already known that certain substituted aryl ketones have herbicidal properties (cf. EP-A-090 262, EP-A-135 191, EP-A-186 118, EP-A-186 119, EP-A-186 120, EP-A-319 075, EP-A-352 543, EP-A-418 175, EP-A-487 357, EP-A-527 036, EP-A-527 037, EP-A-560 483, EP-A-609 797, EP-A-609,798, EP-A-625 505, EP-A-625 508, EP-A-636 622, U.S. Pat. No. 5,804,532, U.S. Pat. No. 5,834,402, U.S. Pat. No. 5,846,906, U.S. Pat. No. 5,863,865, WO-A-95/31466, WO-A-96/26192, WO-A-96/26193, WO-A-96/26200, WO-A-96/26206, WO-A-97/27187, WO-A-97/35850, WO-A-97/41105, WO-A-97/41116, WO-A-97/41117, WO-A-97/41118, WO-A-97/43270, WO-A-97/46530, WO-A-98/28981, WO-A-98/31681, WO-A-98/31682, WO-A-99/03856, WO-A-99/07688, WO-A-99/07697, WO-A-99/10327, WO-A-99/10328, WO-A-00/05221 and in particular WO-A-00/21924). However, the activity of these compounds is not entirely satisfactory.

This invention, accordingly, provides the novel substituted aryl ketones of the formula (I)

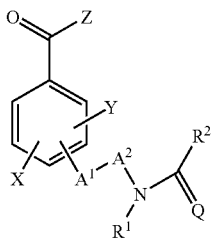

in which
- $A^1$ represents a single bond or represents O (oxygen), S (sulphur), SO or $SO_2$,
- $A^2$ represents alkanediyl (alkylene), alkenediyl or alkinediyl,
- Q represents O (oxygen) or S (sulphur),
- $R^1$ represents hydrogen or represents in each case optionally substituted alkyl, alkoxy, alkylthio, alkylsulphinyl, alkylsulphonyl, alkylamino, dialkylamino, alkenyl, alkinyl, cycloalkyl, cycloalkylalkyl, aryl or arylalkyl, or represents the grouping $-C(Q)-R^2$,
- $R^2$ represents hydrogen, amino, cyanoamino, nitroamino, hydroxyamino, hydrazino, or represents in each case optionally substituted alkyl, alkylcarbonyl, alkoxy, alkoxycarbonyl, alkylthio, alkylamino, dialkylamino, alkoxyamino, N-alkyl-alkoxyamino, alkylhydrazino, dialkylhydrazino, alkenyl, alkenyloxy, alkenylamino, alkenyloxyamino, alkinyl, alkinyloxy, alkinylamino, cycloalkyl, cycloalkyloxy, cycloalkylamino, cycloalkylalkyl, cycloalkylalkoxy, cycloalkylalkylamino, aryl, arylcarbonyl, aryloxy, aryloxycarbonyl, arylthio, arylamino, arylhydrazino, arylalkyl, arylalkoxy, arylalkylthio, arylalkylamino, heterocyclyl, heterocyclyloxy, heterocyclylthio, heterocyclylamino, heterocyclylalkyl, heterocyclylalkoxy, heterocyclylalkylthio or heterocyclylalkylamino,
- X represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl,
- Y represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, and
- Z represents one of the groupings below

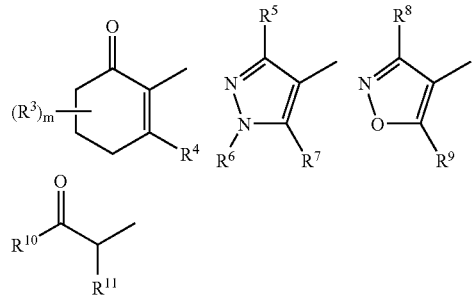

where
- m represents the numbers 0 to 6,
- $R^3$ represents hydrogen, halogen or represents in each case optionally substituted alkyl, alkylthio or aryl, or—if m represents 2—optionally also together with a second radical $R^3$ represents oxygen or alkanediyl (alkylene),
- $R^4$ represents hydroxyl, formyloxy, halogen, or represents in each case optionally substituted alkoxy, alkylthio, alkylsulphinyl, alkylsulphonyl, alkylcarbonyloxy, alkoxycarbonyloxy, alkylaminocarbonyloxy, alkylsulphonyloxy, alkenyloxy, alkinyloxy, aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl or arylalkylsulphonyl,
- $R^5$ represents hydrogen, cyano, carbamoyl, thiocarbamoyl, halogen, or represents in each case optionally substituted alkyl, alkoxy, alkylthio, alkylsulphinyl, alkylsulphonyl, alkoxycarbonyl or cycloalkyl,
- $R^6$ represents hydrogen or represents in each case optionally substituted alkyl, alkenyl, alkinyl, cycloalkyl, cycloalkylalkyl, aryl or arylalkyl,
- $R^7$ represents hydroxyl, formyloxy, or represents in each case optionally substituted alkoxy, alkylcarbonyloxy, alkoxycarbonyloxy, alkylaminocarbonyloxy, alkylsulphonyloxy, alkenyloxy, alkinyloxy, arylalkoxy, arylcarbonyloxy, arylcarbonylalkoxy or arylsulphonyloxy,
- $R^8$ represents hydrogen, cyano, carbamoyl, thiocarbamoyl, halogen, or represents in each case optionally substituted alkyl, alkylcarbonyl, alkoxy, alkoxycarbonyl, alkylthio, alkylsulphinyl or alkylsulphonyl,
- $R^9$ represents hydrogen or represents in each case optionally substituted alkyl or cycloalkyl, R¹⁰ represents hydrogen or represents in each case optionally substituted alkyl or cycloalkyl, and R¹¹ represents hydrogen, cyano, carbamoyl, halogen, or represents in each case optionally substituted alkyl, alkoxy, alkoxycarbonyl, alkylthio, alkylsulphinyl or alkylsulphonyl.

The radical X is preferably located in position (2) of the phenyl ring.

In the definitions, the hydrocarbon chains, such as alkyl or alkanediyl, are in each case straight-chain or branched—including in combination with heteroatoms, such as in alkoxy.

If the compounds of the general formula (I) can exist in different stereoisomeric forms, the invention includes the stereoisomeric forms possible in each case.

Preferred substituents or ranges of the radicals present in the formulae listed above and below are defined below.

A¹ preferably represents O or represents a single bond.

A² preferably represents alkanediyl (alkylene), alkenediyl or alkinediyl having in each case up to 6 carbon atoms.

Q preferably represents O (oxygen).

R¹ preferably represents hydrogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl or alkylamino having in each case 1 to 6 carbon atoms in the alkyl groups, represents dialkylamino having in each case 1 to 4 carbon atoms in the alkyl groups, represents in each case optionally cyano- or halogen-substituted alkenyl or alkinyl having in each case 2 to 6 carbon atoms, represents in each case optionally cyano-, halogen- or $C_1$-$C_4$-alkyl-substituted cycloalkyl or cycloalkylalkyl having in each case 3 to 6 carbon atoms in the cycloalkyl group. and optionally 1 to 4 carbon atoms in the alkyl moiety, represents in each case optionally nitro-, cyano-, halogen-, $C_1$-$C_4$-alkyl-, $C_1$-$C_4$-halogenoalkyl-, $C_1$-$C_4$-alkoxy- or $C_1$-$C_4$-halogenoalkoxy-substituted aryl or arylalkyl having in each case 6 or 10 carbon atoms in the aryl group and optionally 1 to 4 carbon atoms in the alkyl moiety, or represents the grouping —C(Q)-R².

R² preferably represents hydrogen, amino, cyanoamino, nitroamino, hydroxyamino, hydrazino, represents $C_1$-$C_4$-alkyl-carbonyl, represents $C_1$-$C_4$-alkoxy-carbonyl, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylamino, alkoxyamino or alkylhydrazino having in each case 1 to 6 carbon atoms in the alkyl groups, represents dialkylamino, N-alkyl-alkoxyamino or dialkylhydrazino having in each case 1 to 4 carbon atoms in the alkyl groups, represents in each case optionally halogen-substituted alkenyl, alkenyloxy, alkenylamino, alkenyloxyamino, alkinyl, alkinyloxy or alkinylamino having in each case 2 to 6 carbon atoms, represents in each case optionally cyano-, halogen- or $C_1$-$C_4$-alkyl-substituted cycloalkyl, cycloalkyloxy, cycloalkylamino, cycloalkylalkyl, cycloalkylalkoxy or cycloalkylalkylamino having in each case 3 to 6 carbon atoms in the cycloalkyl group and optionally 1 to 4 carbon atoms in the alkyl moiety, represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy- or $C_1$-$C_4$-alkoxy-carbonyl-substituted aryl, arylcarbonyl, aryloxy, aryloxycarbonyl, arylthio, arylamino, arylhydrazino, arylalkyl, arylalkoxy, arylalkylthio or arylalkylamino having in each case 6 or 10 carbon atoms in the aryl group and optionally 1 to 4 carbon atoms in the alkyl moiety, or represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-alkylthio-, $C_1$-$C_4$-halogenoalkylthio- or $C_1$-$C_4$-alkoxy-carbonyl-substituted monocyclic or bicyclic heterocyclyl, heterocyclyloxy, heterocyclylthio, heterocyclylamino, heterocyclylalkyl, heterocyclylalkoxy, heterocyclylalkylthio or heterocyclylalkylamino, where in each case the heterocyclyl grouping contains up to 10 carbon atoms and additionally at least one heteroatom selected from the group consisting of nitrogen (N) (but at most 5 N atoms), oxygen (O) (but at most 2 O atoms), sulphur (S) (but at most 2 S atoms), SO and SO₂ and also optionally additionally one group selected from the group consisting of oxo (C=O), thioxo (C=S), imino (C=NH), cyanoimino (C=N—CN) and nitroimino (C=N—NO₂).

X preferably represents hydrogen, nitro, cyano, carboxyl, carbamoyl, thiocarbamoyl, halogen, or represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups.

Y preferably represents hydrogen, nitro, cyano, carboxyl, carbamoyl, thiocarbamoyl, halogen, or represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups.

Z preferably represents one of the groupings below.

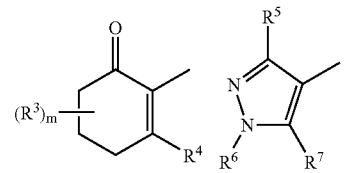

m preferably represents the numbers 0 to 3.

R³ preferably represents hydrogen, halogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl or alkylthio having in each case 1 to 6 carbon atoms, or represents phenyl, or if m represents 2—optionally also together with a second radical R³ represents oxygen or alkanediyl (alkylene) having 3 to 5 carbon atoms.

R⁴ preferably represents hydroxyl, formyloxy, halogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkoxy, alkylthio, alkylsulphinyl, alkylsulphonyl, alkylcarbonyloxy, alkoxycarbonyloxy, alkylaminocarbonyloxy or alkylsulphonyloxy having in each case 1 to 6 carbon atoms, represents in each case optionally halogen-substituted alkenyloxy or alkinyloxy having in each case 3 to 6 carbon atoms, represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkylsulphinyl-, $C_1$-$C_4$-halogenoalkylsulphinyl-, $C_1$-$C_4$-alkylsulphonyl- or $C_1$-$C_4$-halogenoalkylsulphonyl-substituted aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl or arylalkylsulphonyl having in each case 6 or 10 carbon atoms in the aryl group and optionally 1 to 4 carbon atoms in the alkyl moiety.

$R^5$ preferably represents hydrogen, cyano, carbamoyl, thiocarbamoyl, halogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl or alkoxycarbonyl having in each case 1 to 6 carbon atoms in the alkyl groups or represents optionally cyano-, halogen- or $C_1$-$C_4$-alkyl-substituted cycloalkyl having 3 to 6 carbon atoms.

$R^6$ preferably represents hydrogen, represents optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl having 1 to 6 carbon atoms, represents in each case optionally cyano- or halogen-substituted alkenyl or alkinyl having in each case 3 to 6 carbon atoms, represents in each case optionally cyano-, halogen- or $C_1$-$C_4$-alkyl-substituted cycloalkyl or cycloalkylalkyl having in each case 3 to 6 carbon atoms in the cycloalkyl group and optionally 1 to 4 carbon atoms in the alkyl moiety, or represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkylsulphinyl-, $C_1$-$C_4$-halogenoalkylsulphinyl-, $C_1$-$C_4$-alkylsulphonyl- or $C_1$-$C_4$-halogenoalkylsulphonyl-substituted aryl or arylalkyl having in each case 6 or 10 carbon atoms in the aryl group and optionally 1 to 4 carbon atoms in the alkyl moiety.

$R^7$ preferably represents hydroxyl, formyloxy, represents in each case optionally cyano-, halogen- or $C_1$-$C_4$-alkoxy-substituted alkoxy, alkylcarbonyloxy, alkoxycarbonyloxy, alkylaminocarbonyloxy or alkylsulphonyloxy having in each case 1 to 6 carbon atoms in the alkyl groups, represents in each case optionally cyano-, or halogen-substituted alkenyloxy or alkinyloxy having in each case 3 to 6 carbon atoms, or represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkylsulphinyl-, $C_1$-$C_4$-halogenoalkylsulphinyl-, $C_1$-$C_4$-alkylsulphonyl- or $C_1$-$C_4$-halogenoalkylsulphonyl-substituted arylalkoxy, arylcarbonyloxy, arylcarbonylalkoxy or arylsulphonyloxy having in each case 6 or 10 carbon atoms in the aryl group and optionally 1 to 4 carbon atoms in the alkyl moiety.

$R^8$ preferably represents hydrogen, cyano, carbamoyl, thiocarbamoyl, halogen, or represents in each case optionally cyano-, halogen- or $C_1$-$C_4$-alkoxy-substituted alkyl, alkylcarbonyl, alkoxy, alkoxycarbonyl, alkylthio, alkylsulphinyl or alkylsulphonyl having in each case 1 to 6 carbon atoms in the alkyl groups.

$R^9$ preferably represents hydrogen, represents optionally cyano-, halogen- or $C_1$-$C_4$-alkoxy-substituted alkyl, or represents optionally cyano-, halogen- or $C_1$-$C_4$-alkyl-substituted cycloalkyl having 3 to 6 carbon atoms.

$R^{10}$ preferably represents hydrogen, represents optionally cyano-, halogen- or $C_1$-$C_4$-alkoxy-substituted alkyl, or represents optionally cyano-, halogen- or $C_1$-$C_4$-alkyl-substituted cycloalkyl having 3 to 6 carbon atoms.

$R^{11}$ preferably represents hydrogen, cyano, carbamoyl, halogen, or represents in each case optionally cyano-, halogen- or $C_1$-$C_4$-alkoxy-substituted alkyl, alkoxy, alkoxycarbonyl, alkylthio, alkylsulphinyl or alkylsulphonyl having in each case 1 to 6 carbon atoms in the alkyl groups.

$A^2$ particularly preferably represents methylene (—$CH_2$—), ethane-1,1-diyl (—$CH(CH_3)$—), ethane-1,2-diyl (dimethylene, —$CH_2CH_2$—), propane-1,1-diyl (—$CH(C_2H_5)$—), propane-1,2-diyl (—$CH(CH_3)CH_2$—), propane-1,3-diyl (—$CH_2CH_2CH_2$—), butane-1,3-diyl (—$CH(CH_3)CH_2CH_2$—), butane-1,4-diyl (—$CH_2CH_2CH_2CH_2$—), ethenediyl, propenediyl, butenediyl, ethinediyl, propinediyl or butinediyl.

$R^1$ particularly preferably represents hydrogen, represents in each case optionally cyano-, fluorine-, chlorine-, bromine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, methylamino, ethylamino, n- or i-propylamino, n-, i-, s- or t-butylamino, represents dimethylamino or diethylamino, represents in each case optionally fluorine-, chlorine- and/or bromine-substituted ethenyl, propenyl, butenyl, pentenyl, ethinyl, propinyl, butinyl or pentinyl, represents in each case optionally cyano-, fluorine-, chlorine-, bromine-, methyl-, ethyl- or propyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, naphthyl, phenylmethyl, phenylethyl, naphthylmethyl or naphthylethyl or represents the grouping —C(Q)-$R^2$.

$R^2$ particularly preferably represents hydrogen, amino, cyanoamino, nitroamino, hydroxyamino, hydrazino, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, methoxyamino, ethoxyamino, n- or i-propoxyamino, n-, i-, s- or t-butoxyamino, methylhydrazino, ethylhydrazino, n- or i-propylhydrazino, n-, i-, s- or t-butylhydrazino, represents dimethylamino, diethylamino, N-methyl-methoxyamino, dimethylhydrazino or diethylhydrazino, represents in each case optionally fluorine-, chlorine- and/or bromine-substituted ethenyl, propenyl, butenyl, pentenyl, ethinyl, propinyl, butinyl, pentinyl, propenyloxy, butenyloxy, pentenyloxy, propenylthio, butenylthio, pentenylthio, propenylamino, butenylamino, pentenylamino, propenyloxyamino, butenyloxyamino, pentenyloxyamino, ethinyl, propinyl, butinyl, pentinyl, propinyloxy, butinyloxy, pentinyloxy, propinylamino, butinylamino or pentinylamino, represents in each case optionally cyano-, fluorine-, chlorine-, bromine-, methyl-, ethyl- or propyl-substituted cyclopropyl, cyclobutyl, cyclopentyl, cyclohexyl, cyclopropyloxy, cyclobutyloxy, cyclopentyloxy, cyclohexyloxy, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylamino, cyclobutylmethylamino, cyclopentylmethylamino or cyclohexylmethylamino, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, phenylcarbonyl, phenoxy, phenoxycarbonyl, phenylthio, phenylamino, phenylhydrazino, naphthyl, naphthyloxy, naphtylthio, naphthylamino, phenylmethyl, phenylethyl, phenylmethoxy, phenylethoxy, phenylmethylthio, phenylethylthio, phenylmethylamino, phenylethylamino, naphthylmethyl, naphthylethyl, naphthylmethoxy, naphthylethoxy, naphthylmethylamino or naphthylethylamino, or represents in each case optionally nitro-, cyano-, fluorine-, chlorine-, bromine-, methyl-, ethyl-, n- or i-propyl-, n-, i-, s- or t-butyl-, difluoromethyl-, trifluoromethyl-, dichloromethyl-, trichloromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methoxycarbonyl-, ethoxycarbonyl-, n- or i-propoxycarbonyl-substituted monocyclic or bicyclic heterocyclyl, heterocyclyloxy, heterocyclylamino, heterocyclylalkyl, heterocyclylalkoxy or heterocyclylalkylamino from the group consisting of furyl, furyloxy, furylamino, furylmethyl, furylmethoxy, furylmethylamino, thienyl, thienylmethyl, pyrrolidinyl, pyrrolidinylamino, oxopyrrolidinyl, pyrrolyl, indolyl, pyrrolylmethyl, pyrazolyl, pyrazolyloxy, pyrazolylamino, pyrazolylmethyl, imidazolyl, imidazolylmethyl, 2-oxo-1,3-diaza-cyclopentyl, oxazolyl, dihydrooxazolyl (oxazolinyl), isoxazolyl, dihydroisoxazolyl (isoxazolinyl), tetrahydroisoxazolyl (isoxazolidinyl), oxazolylmethyl, thiazolyl, dihydrothiazolyl (thiazolinyl), tetrahydrothiazolyl (thiazolidinyl), thiazolylmethyl, thiazolidinyl, oxothiazolidinyl, cyanoiminothiazolidinyl, oxotriazolinyl, oxotetrazolinyl, piperidinyl, piperidinylamino, oxopiperidinyl, 2-oxo-1,3-diaza-cyclohexyl, 2-oxo-1-aza-cycloheptyl, 2-oxo-1,3-diazacycloheptyl, morpholinyl, morpholinylamino, piperazinyl, pyridinyl, pyridinyloxy, pyridinylamino, pyridinylmethyl, pyridinylmethoxy, pyrimidinyl, pyrimidinyloxy, pyrimidinylmethyl, pyrimidinylmethoxy.

X particularly preferably represents hydrogen, nitro, cyano, carboxyl, carbamoyl, thiocarbamoyl, fluorine, chlorine, bromine, iodine, or represents in each case optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl.

Y particularly preferably represents hydrogen, nitro, cyano, carboxyl, carbamoyl, thiocarbamoyl, fluorine, chlorine, bromine, iodine, or represents in each case optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl.

m particularly preferably represents the number 0, 1 or 2.

$R^3$ particularly preferably represents hydrogen, fluorine, chlorine or bromine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methylthio, ethylthio, n- or i-propylthio, n-, i-, s- or t-butylthio, or represents phenyl, or—if m represents 2,—optionally also together with a second radical $R^3$ represents oxygen, propane-1,3-diyl or butane-1,4-diyl.

$R^4$ particularly preferably represents hydroxyl, formyloxy, fluorine or chlorine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine-, chlorine- and/or bromine-substituted propenyloxy, butenyloxy, propinyloxy or butinyloxy, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenyloxy, phenylthio, phenylsulphinyl, phenylsulphonyl, phenylcarbonyloxy, phenylcarbonylalkoxy, phenylsulphonyloxy, phenylmethoxy, phenylmethylthio, phenylmethylsulphinyl or phenylmethylsulphonyl.

$R^5$ particularly preferably represents hydrogen, cyano, carbamoyl, thiocarbamoyl, fluorine, chlorine or bromine, represents in each case optionally cyano-, fluorine-, chlorine-,, methoxy-, ethoxy-, n- or i-propoxy-, methylthio-, ethylthio-, n-, or i-propylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, or represents in each case optionally cyano-, fluorine-, chlorine-, methyl- or ethyl-substituted cyclopropyl, cyclobutyl, cyclopentyl or cyclohexyl.

$R^6$ particularly preferably represents hydrogen, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally cyano-, fluorine-, chlorine- or bromine-substituted propenyl, butenyl, propinyl or butinyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, n-, i-, s- or t-butylthio-, difluoromethylthio-, trifluoromethylthio-, methylsulphinyl-, ethylsulphinyl-, trifluoromethylsulphinyl-, methylsulphonyl, ethylsulphonyl- or trifluoromethylsulphonyl-substituted phenyl or phenylmethyl.

$R^7$ particularly preferably represents hydroxyl, formyloxy, represents in each case optionally cyano-, fluorine-, chlorine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, or represents in each case optionally cyano-, fluorine-, chlorine- or bromine-substituted propenyloxy, butenyloxy, propinyloxy or butinyloxy, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenylmethoxy, phenylcarbonyloxy, phenylcarbonylmethoxy or phenylsulphonyloxy.

$R^8$ particularly preferably represents hydrogen, cyano, carbamoyl, thiocarbamoyl, fluorine, chlorine or bromine, or represents in each case optionally cyano-, fluorine-, chlorine-, methoxy-, ethoxy-, n- or i-propoxy-substituted methyl, ethyl, n- or i-propyl, n-, i-, s- or t-butyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl.

$R^9$ particularly preferably represents hydrogen, represents in each case optionally cyano-, fluorine-, chlorine-, methoxy-, ethoxy-, n- or i-propoxy-substituted methyl, ethyl, n- or i-propyl, n-, i-, s- or t-butyl, or represents in each case optionally cyano-, fluorine-, chlorine-, methyl- or ethyl-substituted cyclopropyl, cyclobutyl, cyclopentyl or cyclohexyl.

$R^{10}$ particularly preferably represents hydrogen, represents in each case optionally cyano-, fluorine-, chlorine-, methoxy-, ethoxy-, n- or i-propoxy-substituted methyl, ethyl, n- or i-propyl, n-, i-, s- or t-butyl, or represents in each case optionally cyano-, fluorine-, chlorine-, methyl- or ethyl-substituted cyclopropyl, cyclobutyl, cyclopentyl or cyclohexyl.

$R^{11}$ particularly preferably represents hydrogen, cyano, carbamoyl, fluorine, chlorine or bromine or represents in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl.

$A^2$ very particularly preferably represents methylene (—CH$_2$—), ethane-1,2-diyl (dimethylene, —CH$_2$CH$_2$—) or propane-1,3-diyl (—CH$_2$CH$_2$CH$_2$—).

$R^1$ very particularly preferably represents hydrogen, represents in each case optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n- or i-butyl, represents methoxy, ethoxy, n- or i-propoxy, methylthio, ethylthio, n- or i-propylthio, methylamino, ethylamino, n- or i-propylamino, represents dimethylamino, represents in each case optionally fluorine- and/or chlorine-substituted propenyl, butenyl, ethinyl, propinyl or butinyl, represents in each case optionally cyano-, fluorine-, chlorine- or methyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, phenylmethyl or phenylethyl, or represents the grouping —C(Q)-R$^2$.

$R^2$ very particularly preferably represents hydrogen, amino, hydroxyamino, hydrazino, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, methylthio, ethylthio, n- or i-propylthio, methylamino, ethylamino, n- or i-propylamino, methoxyamino, ethoxyamino, n- or i-propoxyamino, represents dimethylamino, represents N-methyl-methoxyamino, represents dimethylhydrazino, represents in each case optionally fluorine- and/or chlorine-substituted ethenyl, propenyl, butenyl, propenyloxy, butenyloxy, propenylthio, butenylthio, propenylamino, butenylamino, ethinyl, propinyl, butinyl, propinyloxy, butinyloxy, propinylamino or butinylamino, represents in each case optionally cyano-, fluorine-, chlorine- or methyl-substituted cyclopropyl, cyclobutyl, cyclopentyl, cyclohexyl, cyclopropylmethyl, cyclobutylmethyl, cyclopentylmethyl or cyclohexylmethyl, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, phenylamino, phenylmethyl or phenylethyl, or represents in each case optionally nitro-, cyano-, fluorine-, chlorine-, bromine-, methyl-, ethyl-, n- or i-propyl-, n-, i-, s- or t-butyl-, difluoromethyl-, trifluoromethyl-, dichloromethyl-, trichloromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methoxycarbonyl-, ethoxycarbonyl-, n- or i-propoxycarbonyl-substituted monocyclic or bicyclic heterocyclyl or heterocyclylalkyl from the group consisting of furyl, furylmethyl, thienyl, thienylmethyl, pyrrolidinyl, oxopyrrolidinyl, pyrrolyl, pyrrolylmethyl, pyrazolyl, pyrazolylmethyl, imidazolyl, imidazolylmethyl, 2-oxo-1,3-diazacyclopentyl, oxazolyl, isoxazolyl, oxazolylmethyl, isoxazolidinyl, thiazolyl, thiazolylmethyl, piperidinyl, oxopiperidinyl, 2-oxo-1,3-diazacyclohexyl, morpholinyl, piperazinyl, pyridinyl, pyridinylmethyl, pyrimidinyl, pyrimidinylmethyl.

X very particularly preferably represents hydrogen, nitro, cyano, fluorine, chlorine, bromine, iodine, methyl, ethyl, n- or i-propyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.

Y very particularly preferably represents hydrogen, nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.

m very particularly preferably represents the number 0 or 1.

$R^3$ very particularly preferably represents hydrogen, represents in each case optionally fluorine- and/or chlorine-substituted methyl, ethyl, n- or i-propyl, methylthio, ethylthio, n- or i-propylthio, or represents phenyl, or—if m represents 2—optionally also together with a second radical $R^3$ represents oxygen, propane-1,3-diyl or butane-1,4-diyl.

$R^4$ very particularly preferably represents hydroxyl, represents formyloxy, represents in each case optionally fluorine- and/or chlorine-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine- and/or chlorine-substituted propenyloxy, butenyloxy, propinyloxy or butinyloxy, represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl or phenylmethylsulphonyl.

$R^5$ very particularly preferably represents hydrogen, cyano, fluorine, chlorine, represents in each case optionally fluorine- and/or chlorine-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, or represents in each case optionally cyano-, fluorine-, chlorine- or methyl-substituted cyclopropyl.

$R^6$ very particularly preferably represents hydrogen, represents in each case optionally cyano-, fluorine-, chlorine-, methoxy or ethoxy-substituted methyl, ethyl, n- or i-propyl, n-, i-, s- or t-butyl, represents in each case optionally fluorine- or chlorine-substituted propenyl, butenyl, propinyl or butinyl, represents in each case optionally fluorine-, chlorine- or methyl-substituted cyclopropyl, cyclobutyl, cyclopentyl or cyclohexyl, or represents in each case optionally fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenyl or phenylmethyl.

$R^7$ very particularly preferably represents hydroxyl, represents formyloxy, represents in each case optionally cyano-, fluorine-, chlorine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine- and/or chlorine-substituted propenyloxy, butenyloxy, propinyloxy or butinyloxy, or represents in each case optionally nitro-, cyano-, fluorine-, chlorine-, bromine-, methyl-, ethyl-, n- or i-propyl-, trifluoromethyl-, methoxy-, ethoxy-, n- or i-propoxy, difluoromethoxy- or trifluoromethoxy-substituted phenylmethoxy, phenylcarbonyloxy, phenylcarbonylmethoxy or phenylsulphonyloxy.

$R^8$ very particularly preferably represents hydrogen, cyano, fluorine, chlorine, bromine, or represents in each case optionally fluorine-, chlorine-, methoxy- or ethoxy-substituted methyl, ethyl, n- or i-propyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl.

$R^9$ very particularly preferably represents hydrogen, represents in each case optionally fluorine-, chlorine-, methoxy- or ethoxy-substituted methyl, ethyl, n- or i-propyl, or represents optionally fluorine-, chlorine- or methyl-substituted cyclopropyl.

$R^{10}$ very particularly preferably represents hydrogen, represents in each case optionally fluorine-, chlorine-, methoxy- or ethoxy-substituted methyl, ethyl, n- or i-propyl, or represents optionally fluorine-, chlorine- or methyl-substituted cyclopropyl.

$R^{11}$ very particularly preferably represents hydrogen, cyano, fluorine, chlorine, bromine, or represents in each case optionally fluorine-, chlorine-, methoxy-, or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl.

$R^1$ most preferably represents hydrogen, or represents in each case optionally fluorine-, chlorine-, methoxy- or ethoxy-substituted methyl, ethyl, n- or i-propyl, represents methoxy or ethoxy or represents the grouping —C(Q)-$R^2$.

$R^2$ most preferably represents hydrogen, amino, hydrazino, or represents in each case optionally fluorine-, chlorine-, methoxy- or ethoxy-substituted methyl, ethyl or n- or i-propyl, represents methylamino, ethylamino, n- or i-propylamino or dimethylamino, represents in each case optionally fluorine-, chlorine- or methyl-substituted cyclopropyl, cyclobutyl, cyclopentyl or cyclohexyl, represents in each case optionally nitro-, cyano-, fluorine-, chlorine-, bromine- methyl-, ethyl- or n- or i-propyl-, methoxy-, ethoxy-, n- or i-propoxy-substituted phenyl, phenylamino, phenylmethyl or phenylethyl, or represents in each case optionally nitro-, cyano-, fluorine-, chlorine-, bromine-, methyl-, ethyl, difluoromethyl-, trifluoromethyl-, dichloromethyl-, trichloromethyl-, chlorodifluoromethyl-, fluorodichloromethyl-, methoxy-, ethoxy-, methylthio-, ethylthio-, difluoromethylthio-, trifluoromethylthio-, methoxycarbonyl- or ethoxycarbonyl-substituted furyl, furylmethyl, thienyl, thienylmethyl, pyrrolyl or pyrrolylmethyl.

X most preferably represents hydrogen, nitro, fluorine, chlorine, bromine, methyl, ethyl or trifluoromethyl.

Y most preferably represents hydrogen, nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.

$R^3$ most preferably represents hydrogen or in each case optionally fluorine- and/or chlorine-substituted methyl or ethyl.

$R^4$ most preferably represents hydroxyl.

$R^5$ most preferably represents hydrogen, fluorine, chlorine or represents in each case optionally fluorine- and/or chlorine-substituted methyl, ethyl, methoxy or ethoxy.

$R^6$ most preferably represents hydrogen or represents in each case optionally fluorine-, chlorine-, methoxy- or ethoxy-substituted methyl, ethyl, n- or i-propyl or n-, i-, s- or t-butyl.

$R^7$ most preferably represents hydroxyl, or represents in each case optionally fluorine-, or chlorine-substituted methoxy or ethoxy, or represents optionally nitro-, cyano-, fluorine-, chlorine-, bromine, methyl-, ethyl-, trifluoromethyl-, methoxy- or ethoxy-substituted phenylmethoxy.

Preference according to the invention is given to the compounds of the formula (I) which contain a combination of the meanings given above as being preferred.

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Most preference according to the invention is given to the compounds of the formula (I) which contain a combination of the meanings given above as being most preferred.

Particular emphasis is given to the compounds of the formulae (I-1) to (I-3):

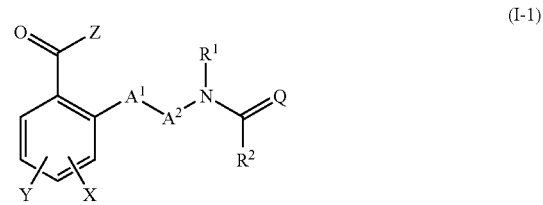

(I-1)

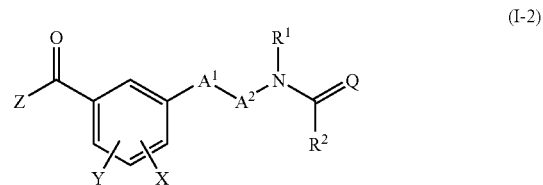

(I-2)

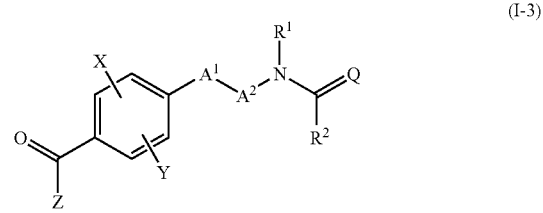

(I-3)

Here, the $A^1$, $A^2$, Q, $R^1$, $R^2$, X, Y and Z each have the meanings given above as being preferred or being very particularly preferred.

Particular emphasis is furthermore given to the compounds of the general formulae (I-2A) to (I-2D):

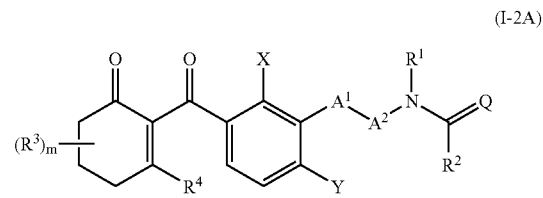

(I-2A)

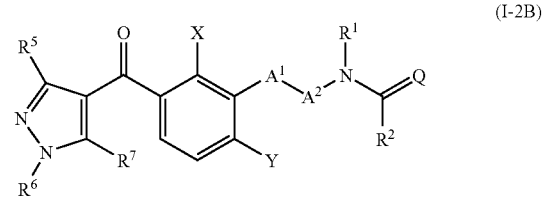

(I-2B)

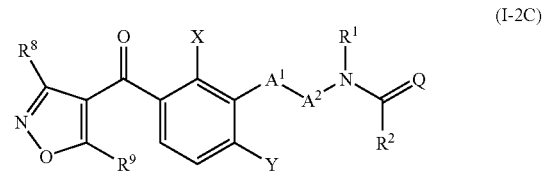

(I-2C)

-continued (I-2D)

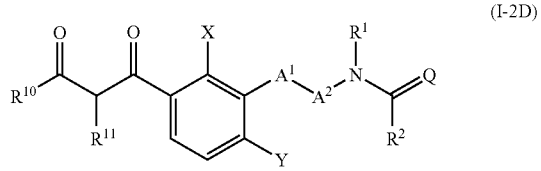

Here, m, $A^1$, $A^2$, Q, $R^1$, $R^2$, $R^3$, $R^4$, $R^5$, $R^6$, $R^7$, $R^8$, $R^9$, $R^{10}$, $R^{11}$, X and Y each have the meanings given above as being preferred or as being very particularly preferred.

Among the compounds of the formulae (I-1) to (I-3) and (I-2A) to (I-2D), very particular emphasis is given to those in which $A^1$ represents a single bond and $A^2$ represents methylene.

Among the compounds of the formulae (I-1) to (I-3) and (I-2A) to (I-2D), very particular emphasis is furthermore also given to those in which $A^1$ represents O (oxygen) and $A^2$ represents ethane-1,2-diyl (dimethylene).

The general or preferred radical definitions given above apply both to the end products of the formula (I) and, correspondingly, to the starting materials or intermediates required in each case for the preparation. These radical definitions can be combined with one another as desired, i.e. including combinations between the given preferred ranges.

The novel substituted aryl ketones of the formula (I) have strong and selective herbicidal activity.

The novel substituted aryl ketones of the formula (I) are obtained when (a) amino compounds of the general formula (II)

(II)

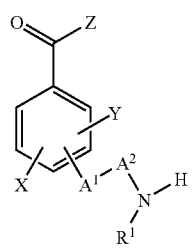

in which
$A^1$, $A^2$, $R^1$, X, Y and Z are as defined above.
are reacted with compounds of the general formula (III)

(III)

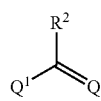

in which
Q and $R^2$ are as defined above and
$Q^1$ represents halogen, alkoxy, alkylthio, aryloxy or arylthio, preferably represents chlorine, bromine, methoxy, ethoxy, methylthio, ethylthio, phenyloxy or phenylthio,
—or, if appropriate, with corresponding iso(thio)cyanates— if appropriate in the presence of one or more reaction auxiliaries and if appropriate in the presence of one or more diluents, or when (b) carboxylic acids of the general formula (IV)

(IV)

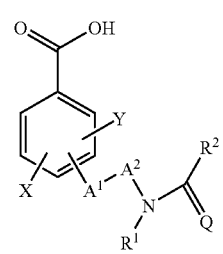

in which
$A^1$, $A^2$, Q, $R^1$, $R^2$, X and Y are as defined above,
—or reactive derivatives thereof, such as, for example, corresponding acid halides, acid cyanides or esters—
are reacted with compounds of the general formula (V)

H-Z (V)

in which
Z is as defined above,
if appropriate in the presence of a dehydrating agent and also, if appropriate in the presence of one or more reaction auxiliaries and, if appropriate, in the presence of one or more diluents, or when (c) substituted benzoyl ketones of the general formula (Ia)

(Ia)

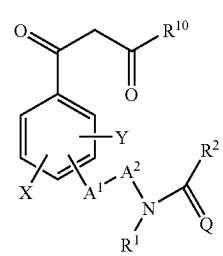

in which
$A^1$, $A^2$, Q, $R^1$, $R^2$, $R^{10}$, X and Y are as defined above,
are reacted with an orthoformic ester or with a N,N-dimethyl-formamide acetal or with a cyanoformic ester or with carbon disulphide and an alkylating agent and subsequently with hydroxylamine or an acid adduct thereof,
if appropriate in the presence of one or more reaction auxiliaries and if appropriate in the presence of one or more diluents, or when
(d) aryl ketones of the general formula (VI)

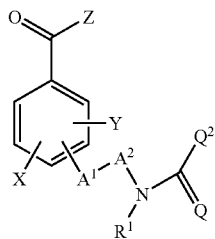 (VI)

in which
A¹, A², Q, R¹, X, Y and Z are as defined above and
Q² represents halogen, alkoxy, alkylthio, aryloxy or arylthio, preferably represents chlorine, bromine, methoxy, ethoxy, methylthio, ethylthio, phenyloxy or phenylthio,
—or, if appropriate, corresponding iso(thio)cyanates—
are reacted with compounds of the general formula (VII)

H—R²  (VII)

in which
R² is as defined above,
if appropriate in the presence of one or more reaction auxiliaries and if appropriate in the presence of one or more diluents,
and following the practice of the process (a), (b), (c) or (d) according to the invention, the resulting compounds of the general formula (I) are, if appropriate and within the bounds of the definition of substituents, subjected to subsequent reactions (for example, substition, oxidation or reduction reactions) according to customary methods for conversion into other compounds of the general formula (I).

Using, for example, [3-(2-amino-ethoxy)-2-chloro-4-methylthio-phenyl]-(5-ethyl-4-isoxazolyl)-methanone and propionyl chloride as starting materials, the course of the reaction in the process (a) according to the invention can be illustrated by the following equation:

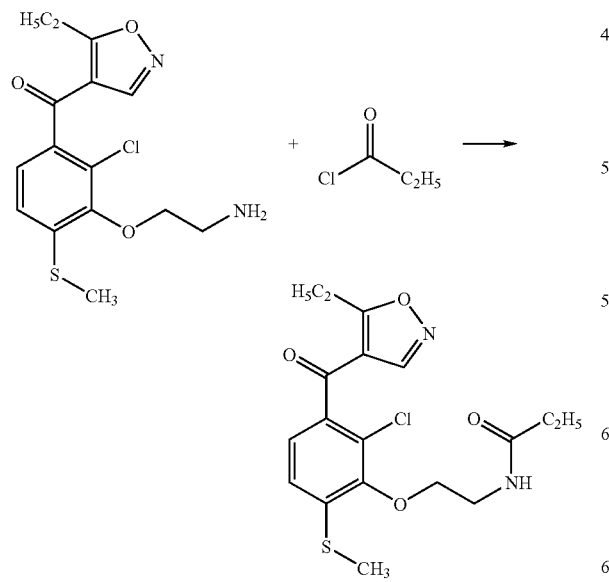

Using, for example, 4-bromo-3-[[(1-pyrrolidinylthioxomethyl)-amino]-methyl]-benzoic acid and cyclohexane-1,3-dione as starting materials, the course of the reaction in the process (b) according to the invention can be illustrated by the following equation:

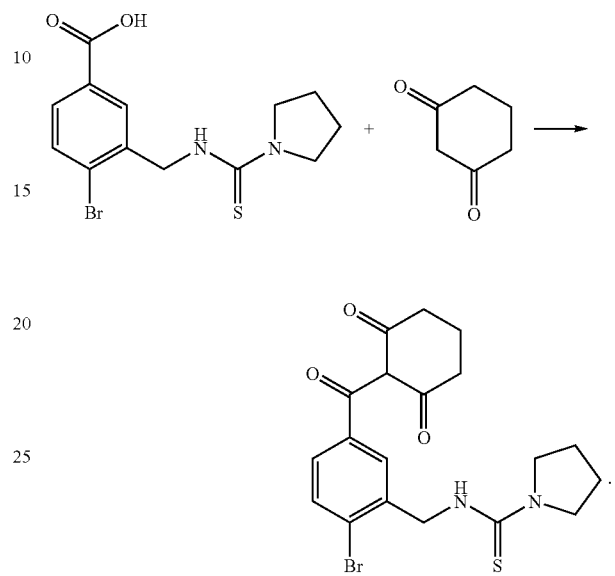

Using, for example, N-[2-chloro-5-(3-cyclopropyl-3-oxopropanoyl)-benzyl]-acetamide, N,N-dimethyl-formamide diethyl acetal and hydroxylamine as starting materials, the course of the reaction in the process (c) according to the invention can be illustrated by the following equation:

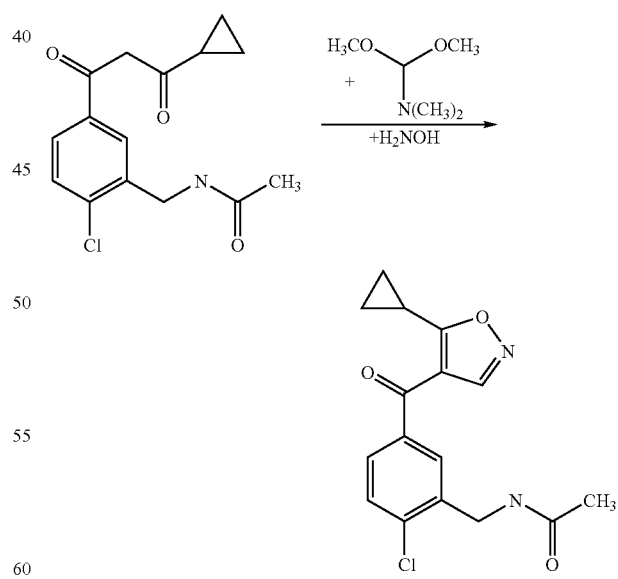

Using, for example, O-methyl N-[[2-bromo-5-[(5-hydroxy-1-methyl-1H-pyrazol-4-yl)-carbonyl]-phenyl]-methyl]-carbamate and pyrrolidine as starting materials, the course of the reaction of the process (d) according to the invention can be illustrated by the following equation:

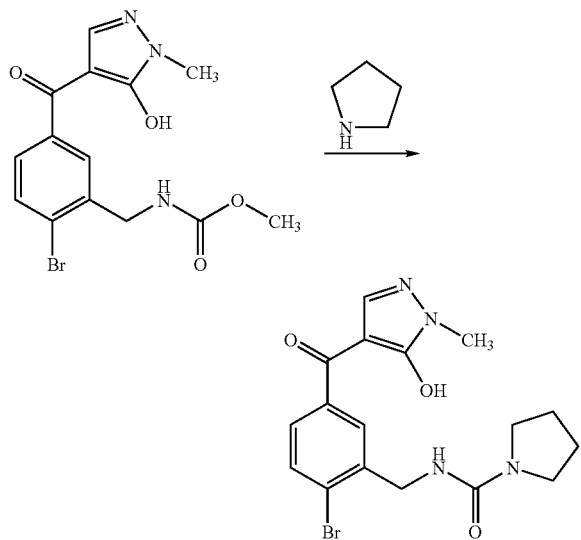

The formula (II) provides a general definition of the amino compounds to be used as starting materials in the process (a) according to the invention for preparing compounds of the general formula (I). In the general formula (II), $A^1$, $A^2$, $R^1$, X, Y and Z preferably have those meanings which have already been mentioned above, in connection with the description of the compounds of the general formula (I) according to the invention, as being preferred, particularly preferred, very particularly preferred or most preferred for $A^1$, $A^2$, $R^1$, X, Y and Z.

The starting materials of the general formula (II) have hitherto not been disclosed in the literature; as novel substances, they also form part of the subject-matter of the present application.

The novel amino compounds of the general formula (II) are obtained when halogen compounds of the general formula (VIII)

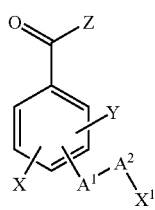

(VIII)

in which
$A^1$, $A^2$, X, Y and Z are as defined above and
$X^1$ represents halogen (preferably fluorine, chlorine, bromine or iodine, in particular chlorine or bromine), are reacted with ammonia or amino compounds of the general formula (IX)

(IX)

in which
$R^1$ is as defined above, if appropriate in the presence of a diluent, such as, for example, tetrahydrofuran, and if appropriate under elevated pressure, at temperatures between 0° C. and 100° C. (cf. the Preparation Examples).

The intermediates of the general formula (VIII) are known and/or can be prepared by processes known per se (cf. WO-A-95/31446, WO-A-00/68227, Preparation Examples).

The intermediates of the general formula (IX) are known chemicals for synthesis.

The formula (III) provides a general definition of the (thi) oxo compounds further to be used as starting materials in the process (a) according to the invention for preparing compounds of the general formula (I). In the general formula (III), Q and $R^3$ preferably have those meanings which have already been given above, in connection with the description of the compounds of the general formula (I) according to the invention, as being preferred, particularly preferred, very particularly preferred or most preferred for Q and $R^3$; $Q^1$ preferably represents fluorine, chlorine, bromine, $C_1$-$C_4$-alkoxy, $C_1$-$C_4$-alkylthio, phenoxy or phenylthio, in particular chlorine, methoxy, ethoxy or phenoxy.

The starting materials of the general formula (III) are known organic chemicals for synthesis.

The formula (IV) provides a general definition of the carboxylic acids to be used as starting materials in the process (b) according to the invention for preparing compounds of the general formula (I). In the general formula (IV), $A^1$, $A^2$, Q, $R^1$, $R^2$, X and Y preferably have those meanings which have already been given above, in connection with the description of the compounds of the general formula (I) according to the invention, as being preferred, particularly preferred, very particularly preferred or most preferred for $A^1$, $A^2$, Q, $R^1$, $R^2$, X and Y.

The starting materials of the general formula (IV) have hitherto not been disclosed in the literature; as novel substances, they also form part of the subject-matter of the present application.

The novel carboxylic acids of the general formula (IV) are obtained when (α) iso(thio)cyanates of the general formula (X)

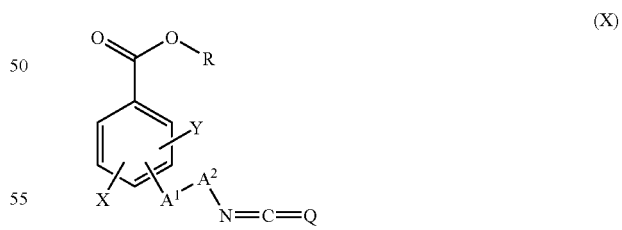

(X)

in which
$A^1$, $A^2$, Q, X and Y are as defined above and
R represents hydrogen, an alkali metal or an alkaline earth metal equivalent (preferably sodium or potassium) or alkyl (preferably $C_1$-$C_4$-alkyl, in particular methyl or ethyl), are reacted with compounds of the general formula (VII)

H—$R^2$ (VII)

in which

R² is as defined above, if appropriate in the presence of a diluent, such as, for example, acetonitrile or ethanol, at temperatures between 0° C. and 100° C., followed, if appropriate, by an ester hydrolysis using customary methods (cf. the Preparation Examples), or when (β) amino compounds of the general formula (XI)

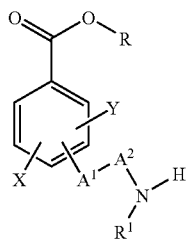

in which

A¹, A², R¹, X and Y are as defined above and

R represents hydrogen, an alkali metal or an alkaline earth metal equivalent (preferably sodium or potassium) or alkyl (preferably $C_1$-$C_4$-alkyl, in particular methyl or ethyl), are reacted with (thi)oxo compounds of the general formula (III)

in which

Q and R² are as defined above and

Q¹ represents halogen, alkoxy, alkylthio, aryloxy or arylthio, preferably chlorine, bromine, methoxy, ethoxy, methylthio, ethylthio, phenyloxy or phenylthio, —or, if appropriate, with corresponding iso(thio)cyanates— if appropriate in the presence of one or more reaction auxiliaries, such as, for example, potassium carbonate or triethylamine, and if appropriate in the presence of one or more diluents, such as, for example, acetonitrile or N,N-dimethyl-formamide, at temperatures between 0° C. and 100° C.

The formula (V) provides a general definition of the compounds further to be used as starting materials in the process (b) according to the invention for preparing compounds of the general formula (I). In the general formula (V), Z preferably has that meaning which has already been given above, in connection with the description of the compounds of the general formula (I) according to the invention, as being preferred, particularly preferred, very particularly preferred or most preferred for Z. The starting materials of the general formula (V) are known organic chemicals for synthesis.

The formula (Ia) provides a general definition of the substituted benzoyl ketones to be used as starting materials in the process (c) according to the invention for preparing compounds of the general formula (I). In the general formula (Ia), A¹, A², Q, R¹, R², R¹⁰, X and Y preferably have those meanings which have already been mentioned above, in connection with the description of the compounds of the general formula (I) according to the invention, as being preferred, particularly preferred, very particularly preferred or most preferred for A¹, A², Q, R¹, R², R¹, X and Y.

As novel substances, the starting materials of the general formula (Ia) also form part of the subject-matter of the present application; they can be prepared by the process (a) or (b) according to the invention.

The formula (VI) provides a general definition of the aryl ketones to be used as starting materials in the process (d) according to the invention for preparing compounds of the general formula (I). In the general formula (VI), A¹, A², Q, R¹, X, Y and Z preferably have those meanings which have already been mentioned above, in connection with the description of the compounds of the general formula (I) according to the invention, as being preferred, particularly preferred, very particularly preferred or most preferred for A¹, A², Q, R¹, X, Y and Z; Q² preferably represents fluorine, chlorine, bromine, $C_1$-$C_3$-alkoxy, $C_1$-$C_3$-alkylthio, phenoxy or phenylthio, in particular chlorine, methoxy, ethoxy or phenoxy.

The starting materials of the formula (VI) can be prepared by processes known to the person skilled in the art.

The formula (VII) provides a general definition of the compounds further to be used as starting materials in the process (d) according to the invention for preparing compounds of the general formula (I). In the general formula (VII), R² preferably has that meaning which has already been mentioned above, in connection with the description of the general formula (I), as being preferred, particularly preferred, very particularly preferred or most preferred for R².

The starting materials of the general formula (VII) are known organic compounds.

The formula (X) provides a general definition of the iso(thio)cyanates to be used as starting materials in the process (a) according to the invention for preparing compounds of the general formula (IV). In the general formula (X), A¹, A², Q, X and Y preferably have that meaning which has already been mentioned above, in connection with the description of the general formula (I), as being preferred, particularly preferred, very particularly preferred or most preferred for A¹, A², Q, X and Y.

The starting materials of the general formula (X) can be obtained by processes known to the person skilled in the art.

The formula (XI) provides a general definition of the amino compounds to be used as starting materials in the process (β) according to the invention for preparing compounds of the general formula (IV). In the general formula (XI), A¹, A², R¹, X and Y preferably have that meaning which has already been mentioned above, in connection with the description of the general formula (I), as being preferred, particularly preferred, very particularly preferred or most preferred for A¹, A², R¹, X and Y.

The starting materials of the general formula (XI) can be prepared by processes known to the person skilled in the art.

The process (a), (b), (c) and (d) according to the invention are preferably carried out using one or more reaction auxiliaries. Suitable reaction auxiliaries for the processes (a), (b), (c) and (d) according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate, or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methyl-pyridine, 4-dimethylamino-pyridine, N-methylpiperidine, N-ethyl-piperidine, N-methyl-morpholine, N-ethyl-morpholine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Further reaction auxiliaries suitable for the processes (a), (b), (c) and (d) according to the invention are phase-transfer catalysts. Examples of such catalysts which may be mentioned are:

Tetrabutylammonium bromide, tetrabutylammonium chloride, tetraoctylammonium chloride, tetrabutylammonium hydrogensulphate, methyl-trioctylammonium chloride, hexadecyl-trimethylammonium chloride, hexadecyl-triethylammonium bromide, benzyl-trimethylammonium chloride, benzyl-triethylammonium chloride, benzyl-trimethylammonium hydroxide, benzyl-triethylammonium hydroxide, benzyl-tributylammonium chloride, benzyl-tributylammonium bromide, tetrabutylphosphonium bromide, tetrabutylphosphonium chloride, tributyl-hexadecylphosphonium bromide, butyl-triphenylphosphonium chloride, ethyl-trioctylphosphonium bromide, tetra-phenylphosphonium bromide.

The process (b) according to the invention for preparing the novel substituted aryl ketones of the general formula (I) is, if appropriate, carried out using a dehydrating agent. Here, suitable dehydrating agents are the chemicals customarily suitable for binding water.

Examples which may be mentioned are dicyclohexylcarbodiimide, carbonyl-bis-imidazole and propanephosphonic anhydride.

Dehydrating agents which may be mentioned as being particularly suitable are dicyclohexcylcarbodimide and propanephosphonic anhydride.

The processes according to the invention for preparing the compounds of the general formula (I) are preferably carried out using diluents. Suitable diluents for carrying out the processes (a), (b), (c) and (d) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether, ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate; sulphoxides, such as dimethyl sufoxide; alcohols, such as methanol, ethanol, n- or i-propanol, ethylene glycol monomethyl ether, ethylene glycol monoethyl ether, diethylene glycol monomethyl ether, diethyleneglycol monoethyl ether, mixtures thereof with water or pure water.

When carrying out the processes (a), (b), (c) and (d) according to the invention, the reaction temperatures can be varied within a relatively wide range. In general, the processes are carried out at temperatures between 0° C. and 150° C., preferably between 10° C. and 120° C.

The process according to the invention is generally carried out under atmospheric pressure. However, it is also possible to carry out the processes according to the invention under elevated or reduced pressure—in general between 0.1 bar and 10 bar.

For carrying out the processes according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

As already mentioned above, it is possible to treat all plants and their parts according to the invention. In a preferred embodiment, wild plants (weeds, harmful plants) and/or plant species and plant cultivars (crop plants) obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Plant cultivars are to be understood as meaning crop plants having certain properties ("traits") which have been obtained by conventional breeding, by mutagenesis or by recombinant DNA techniques. They can be cultivars, bio- or genotypes.

The transgenic plants or plant cultivars (i.e. those obtained by genetic engineering) which are treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (including rice), maize, soya beans, potatoes, cotton, beets, cultivated grasses such as golfing greens and ornamental lawns, oilseed rape, fruit plants (with the fruits apples, pears, citrus fruits and grapes), and plantation crops, such as oil and rubber trees, where particular emphasis is given to cereals including rice), maize, soya beans, potatoes, cotton, beets and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA (b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds and classes of active compounds, such as glyphosate or glufosinate/phosphinotricin (for example the "PAT" gene), ALS inhibitors, such as imidazolinones, sulphonylureas and others, PPO inhibitors (for example plants having Acuron genes), 4-HPD inhibitors, such as isozazoles (for example isoxaflutole), ACCase inhibitors, such as sethoxydim, and also bromoxynil. The genes which impart the desired traits in question can also be present in combinations with one another in the transgenic plants. Examples of "Bt plants" which may be mentioned are maize cultivars, cotton cultivars, soya bean cultivars and potato cultivars which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize cultivars, cotton cultivars, soya bean cultivars, cereal cultivars including rice cultivars, beet cultivars and oilseed rape cultivars which are sold under the trade names Roundup Ready® (tolerance to glyphosate, for example maize, cotton, soya bean, beets, oilseed rape), Liberty Link® (tolerance to glufosinate, for example oilseed rape, maize, beets), IMI® (tolerance to imidazolinones) and STS® (tolerance to sulphonylureas, for example maize). Herbicide-resistant plants (plants bred in a conventional manner for herbicide tolerance) which may be mentioned include the cultivars sold under the name Clearfield® (for example maize, rice).

Of course, these statements also apply to plant cultivars having these genetic traits or genetic traits still to be developed, which plants will be developed and/or marketed in the future.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention—also in combination with other agrochemical active compounds—, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The plants listed can be treated according to the invention in a particularly advantageous manner with the compounds of the general formula (I) or the active compound mixtures according to the invention where in addition to the good control of weed plants, the abovementioned synergistic effects with the transgenic plants or plant cultivars occur. The preferred ranges stated above for the active compounds or mixtures also apply to the treatment of these plants. Particular emphasis is given to the treatment of plants with the compounds or mixtures specifically mentioned in the present text.

The treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic minerals such as highly-disperse silica, alumina and silicates; suitable solid carriers for granules are: for example crushed and fractionated natural rocks such as calcite, marble, pumice, sepiolite and dolomite, or else synthetic granules of inorganic and organic minerals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Suitable components for the mixtures are known herbicides, for example acetochlor, acifluorfen (-sodium), aclonifen, alachlor, alloxydim (-sodium), ametryne, amicarbazone, amidochlor, amidosulfuron, amitrole, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromacil, bromobutide, bromofenoxim, bromoxynil, butachlor, butafenacil (-allyl), butenachlor, butralin, butroxydim, butylate, cafenstrole, carbetamide, carfentrazone (-ethyl), chlomethoxyfen, chloramben, chloridazon, chlorimuron (-ethyl), chlomitrofen, chlorsulfuron, chlorthiamid, chlortoluron, cinidon (-ethyl), cinmethylin, cinosulfuron, clefoxydim, clethodim, clodinafop (-propargyl), clomazone, clomeprop, clopyralid, cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlobenil, dichlorprop (—P), diclofop (-methyl), diclosulam, diethatyl (-ethyl), difenopenten (-ethyl), difenzoquat, diflufenican, diflufenzopyr, dikegulac (-sodium), dimefuron, dimepiperate, dimethachlor, dimethametryn, dimethenamid, dimexyflam, dinitramine, diphenamid, diquat (-dibromide), dithiopyr, diuron, dymron, epropodan, EPTC, esprocarb, ethalfluralin, ethametsulfuron (-methyl), ethiozin, ethofumesate, ethoxyfen, ethoxysulfuron, etobenzanid, fenoxaprop (—P-ethyl), fentrazamide, flamprop (-M-isopropyl, -M-methyl), flazasulfuron, florasulam, fluazifop (—P-butyl), fluazolate, flucarbazone (-sodium), fluchloralin, flufenacet, flumetsulam, flumiclorac (-pentyl), flumioxazin, flumipropyn, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fomesafen, foramsulfuron, glufosinate (-ammonium), glyphosate (-ammonium, -isopropylammonium), halosafen, halosulfuron (-methyl), haloxyfop (-ethoxyethyl, —P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxadifen (-ethyl), isoxaflutole, isoxapyrifop, ketospiradox, lactofen, lenacil, linuron, MCPA, mecoprop (—P), mefenacet, mesotrione, metamitron, metazachlor, methabenzthiazuron, methyldymron, metobenzuron, metobromuron, (S—) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, pethoxamid, phenmedipham, picolinafen, piperophos, pretilachlor, primisulfuron (-methyl), profluazol, profoxydim, prometryn, propachlor, propanil, propaquizafop, propisochlor, propoxycarbazone (-sodium), propyzamide, prosulfocarb, prosulfiron, pyraflufen (-ethyl), pyrazogyl, pyrazolate, pyrazosulfuron (-ethyl), pyrazoxyfen, pyribenzoxim, pyributicarb, pyridafol, pyridate, pyridatol, pyriftalid, pyriminobac (-methyl), pyrithiobac (-sodium), quinchlorac, quinmerac, quinoclamine, quizalofop (—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (—P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

PREPARATION EXAMPLES

Example 1

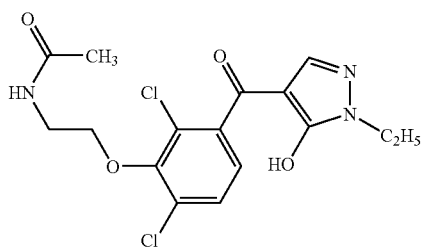

(Process (a))

0.28 g (3.6 mmol) of acetyl chloride is added to a suspension of 1.0 g (2.9 mmol) of [3-(2-aminoethoxy)-2,4-dichlorophenyl]-(1-ethyl-5-hydroxy-1H-pyrazol-4-yl)-methanone and 0.8 g (5.8 mmol) of potassium carbonate in 6 ml of acetonitrile, and the reaction mixture is stirred at room temperature (about 20° C.) for 24 hours. The solvent is then removed under reduced pressure and the residue is dissolved in a little water. The aqueous solution is washed with dichloromethane and then acidified with conc. hydrochloric acid and extracted with ethyl acetate. The organic phase is washed with saturated aqueous sodium chloride solution, dried over sodium sulphate and filtered. From the filtrate, the solvent is carefully distilled off under reduced pressure.

This gives 0.8 g (71.5% of theory) of N-(2-{2,6-dichloro-3-[(1-ethyl-5-hydroxy-1H-pyrazol-4-yl)-carbonyl]-phenoxy}-ethyl)-acetamide (Example I-2-1) as an orange-yellow glass-like solid.

log P=1.41.

Example 2

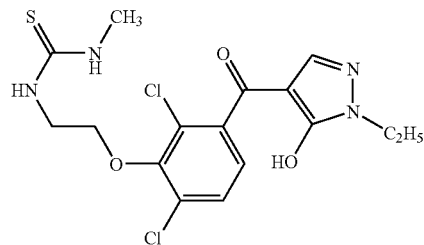

(Process (a))

0.24 g (3.3 mmol) of methyl isothiocyanate is added to a suspension of 0.5 g (1.45 mmol) of [3-(2-amino-ethoxy)-2,4-dichloro-phenyl]-(1-ethyl-5-hydroxy-1H-pyrazol-4-yl)-methanone in 10 ml of methanol, and the reaction mixture is heated at the boil under reflux for 24 hours. Water and ethyl acetate are added and the organic phase is then separated off, washed with saturated aqueous sodium chloride solution, dried over sodium sulphate and filtered. From the filtrate, the solvent is carefully distilled off under reduced pressure.

This gives 0.55 g (91% of theory) of N-(2-{2,6-dichloro-3-[(1-ethyl-5-hydroxy-1H-pyrazol-4-yl)-carbonyl]-phenoxy}-ethyl)-N'-methyl-thiourea (Example I-2-2) as an orange-yellow viscous oil.

log P=1.60.

Example 3

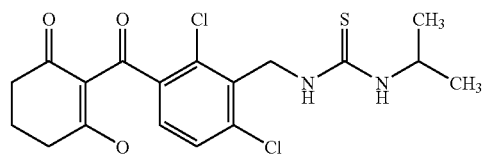

(Process (b))

0.7 g (6.25 mmol) of 1,3-cyclohexanedione and 2.0 g (6.25 mmol) of N-(3-carboxyl-2,6-dichloro-benzyl)-N'-isopropyl-thiourea are initially charged to 50 ml of acetonitrile. 1.5 g (7.25 mmol) of dicyclohexylcarbodiimide are added and the mixture is stirred at room temperature (about 20° C.) for 15 hours. 0.7 g (7 mmol) of triethylamine and 0.7 g (8 mmol) of 2-hydroxy-2-methyl-propionitrile is then added, and the mixture is stirred at room temperature for another 15 hours. The mixture is then stirred with 50 ml of aqueous 1M potassium carbonate solution and filtered off with suction, and the filtrate is acidified to pH 4 using hydrochloric acid. The mixture is extracted three times with in each case 30 ml of dichloromethane and the combined organic phases are dried with magnesium sulphate and filtered. The solvent is then removed under reduced pressure.

This gives 1.1 g (30% of theory) of N-(3-(cyclohex-1-en-2-ol-6-on-1-ylcarbonyl)-2,4-dichlorobenzyl)-N'-isopropyl-thiourea (Example I-2-3) as an oily residue.

log P=2.74.

Example 4

(Subsequent Reaction)

0.25 g (1.0 mmol) of 1-bromo-4-(bromomethyl)-benzene and 0.15 g of 1,8-diazabicyclo-(5.4.0)-undec-7-en (DBU) are added to a solution of 0.193 g (0.5 mmol) of N-(2-{2,6-dichloro-3-[(1-ethyl-5-hydroxy-1H-pyrazol-4-yl)-carbonyl]-phenoxy}-ethyl)-acetamide in 6 ml of toluene, and the reaction mixture is heated at the boil under reflux for 9 hours. The supernatant toluene phase is decanted off and the oily residue that remains is separated by column chromatography using the mobile phase dichloromethane/methanol (9:1).

This gives 0.12 g (43% of theory) of N-{2-[3-({5-[(4-bromo-benzyl)-oxy]-1-ethyl-1H-pyrazol-4-yl}-carbonyl)-2,6-dichloro-phenoxy]-ethyl}-acetamide (Example I-2-4) as a yellow viscous oil.

log P=2.06.

Analogously to Examples 1 to 4 and in accordance with the general description of the preparation processes according to the invention, it is also possible to prepare, for example, the compounds of the general formula (I)—or of the formulae (I-1) to (I-3) or the formulae (I-2a) to (I-2d)—listed in Table 1 below.

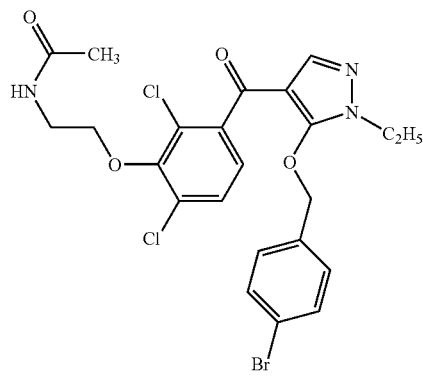

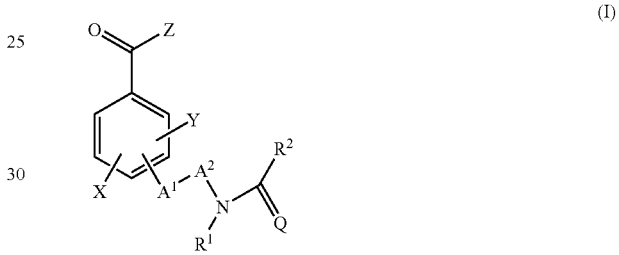

(I)

TABLE 1

Examples of compounds of the formula (I-2)

(I-2)

| Ex. No. | $A^1$ | $A^2$ | Q | $R^1$ | $R^2$ | (position) X | (position) Y | Z | Physical data |
|---|---|---|---|---|---|---|---|---|---|
| I-2-5 | O | (CH$_2$)$_2$ | O | H | H$_2$C–O–CH$_3$ | (2) Cl | (4) Cl | pyrazole (1-ethyl, 5-OH) | log P = 1.64[a] |
| I-2-6 | O | (CH$_2$)$_2$ | O | H | cyclopropyl | (2) Cl | (4) Cl | pyrazole (1-ethyl, 5-OH) | log P = 1.78[a] |

TABLE 1-continued
Examples of compounds of the formula (I-2)
(I-2)
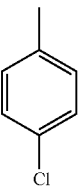
| Ex. No. | A¹ | A² | Q | R¹ | R² | (position) X | (position) Y | Z | Physical data |
|---|---|---|---|---|---|---|---|---|---|
| I-2-7 | O | (CH$_2$)$_2$ | O | H | 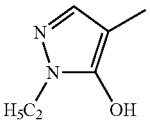 | (2) Cl | (4) Cl | 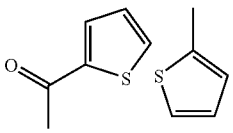 | log P = 2.63[a)] |
| I-2-8 | O | (CH$_2$)$_2$ | O | | 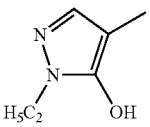 | (2) Cl | (4) Cl | 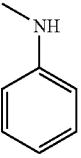 | |
| I-2-9 | — | CH$_2$ | S | H | 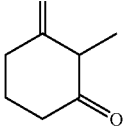 | (2) Cl | (4) Cl |  | log P = 3.05[a)] |
| I-2-10 | — | CH$_2$ | O | C$_3$H$_7$-i | 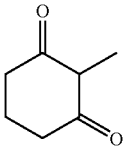 | (2) Cl | (4) Cl |  | log P = 2.86[a)] |
| I-2-11 | — | CH$_2$ | O | C$_3$H$_7$-i | 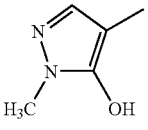 | (2) Cl | (4) Cl | 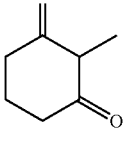 | log P = 2.02[a)] |
| I-2-12 | — | CH$_2$ | O | C$_3$H$_7$-i | NH$_2$ | (2) Cl | (4) Cl | 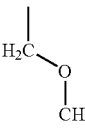 | log P = 2.03[a)] |
| I-2-13 | O | (CH$_2$)$_2$ | O | H | 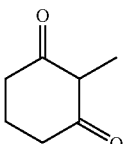 | (2) Cl | (4) Cl | 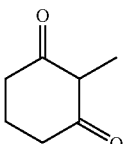 | log P = 2.12[a)] |
| I-2-14 | — | CH$_2$ | O | C$_3$H$_7$-i | NH$_2$ | (2) Cl | (4) Cl | 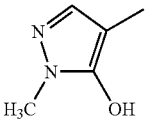 | log P = 1.32[a)] |

TABLE 1-continued
Examples of compounds of the formula (I-2)
| Ex. No. | A¹ | A² | Q | R¹ | R² | (position) X | (position) Y | Z | Physical data |
|---|---|---|---|---|---|---|---|---|---|
| I-2-15 | — | CH$_2$ | O | C$_3$H$_7$-i | 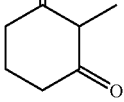 | (2) Cl | (4) Cl |  | log P = 2.33[a] |
| I-2-16 | — | CH$_2$ | O | C$_3$H$_7$-i | 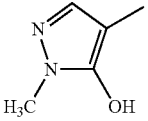 | (2) Cl | (4) Cl | 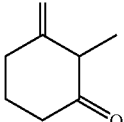 | log P = 1.42[a] |
| I-2-17 | — | CH$_2$ | O | C$_3$H$_7$-i | N(CH$_3$)$_2$ | (2) Cl | (4) Cl | 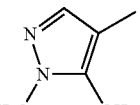 | log P = 2.82[a] |
| I-2-18 | — | CH$_2$ | O | C$_3$H$_7$-i | N(CH$_3$)$_2$ | (2) Cl | (4) Cl | 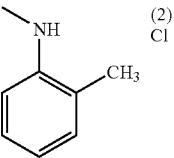 | log P = 2.00[a] |
| I-2-19 | — | CH$_2$ | O | H | 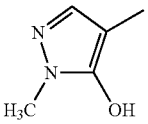 | (2) Cl | (4) Cl |  | log P = 1.95[a] |
| I-2-20 | — | CH$_2$ | O | H | 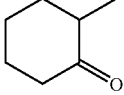 | (2) Cl | (4) Cl | 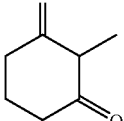 | log P = 1.87[a] |
| I-2-21 | — | CH$_2$ | O | H | N(CH$_3$)$_2$ | (2) Cl | (4) Cl |  | log P = 1.87[a] |
| I-2-22 | — | CH$_2$ | O | H | 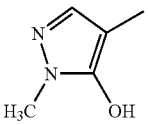 | (2) Cl | (4) Cl |  | log P = 1.35[a] |

TABLE 1-continued

Examples of compounds of the formula (I-2)

(I-2)

| Ex. No. | A¹ | A² | Q | R¹ | R² | X (position) | Y (position) | Z | Physical data |
|---|---|---|---|---|---|---|---|---|---|
| I-2-23 | — | CH$_2$ | O | H | N(CH$_3$)$_2$ | (2) Cl | (4) Cl | 1-methyl-5-hydroxypyrazol-4-yl | log P = 1.13[a] |
| I-2-24 | — | CH$_2$ | O | cyclopropyl | N(CH$_3$)$_2$ | (2) Cl | (4) Cl | 2-methyl-1,3-cyclohexanedion-yl | log P = 2.45[a] |
| I-2-25 | — | CH$_2$ | O | 4-chlorophenyl | N(CH$_3$)$_2$ | (2) Cl | (4) Cl | 1-methyl-5-hydroxypyrazol-4-yl | log P = 1.69[a] |
| I-2-26 | — | CH$_2$ | O | phenyl | NH-C$_3$H$_7$-i | (2) Cl | (4) Cl | 2-methyl-1,3-cyclohexanedion-yl | |
| I-2-27 | — | CH$_2$ | O | phenyl | NH-C$_3$H$_7$-i | (2) Cl | (4) Cl | 1-methyl-5-hydroxypyrazol-4-yl | |
| I-2-28 | — | CH$_2$ | O | phenyl | NH-CH$_3$ | (2) Cl | (4) Cl | 2-methyl-1,3-cyclohexanedion-yl | |
| I-2-29 | — | CH$_2$ | O | phenyl | NH-CH$_3$ | (2) Cl | (4) Cl | 1-methyl-5-hydroxypyrazol-4-yl | |

TABLE 1-continued

Examples of compounds of the formula (I-2)

(I-2)

| Ex. No. | A¹ | A² | Q | R¹ | R² | (position) X | (position) Y | Z | Physical data |
|---|---|---|---|---|---|---|---|---|---|
| I-2-30 | — | CH$_2$ | O | H | NHCH$_3$ | (2) Cl | (4) Cl | 2-methylcyclohexane-1,3-dione | |
| I-2-31 | — | CH$_2$ | O | H | NHCH$_3$ | (2) Cl | (4) Cl | 1,4-dimethyl-5-hydroxypyrazole | |
| I-2-32 | — | CH$_2$ | O | H | pyrrolidinyl | (2) Cl | (4) Cl | 2-methylcyclohexane-1,3-dione | |
| I-2-33 | — | CH$_2$ | O | H | pyrrolidinyl | (2) Cl | (4) Cl | 1,4-dimethyl-5-hydroxypyrazole | |
| I-2-34 | — | CH$_2$ | O | H | piperidinyl | (2) Cl | (4) Cl | 2-methylcyclohexane-1,3-dione | |
| I-2-35 | — | CH$_2$ | O | H | piperidinyl | (2) Cl | (4) Cl | 1,4-dimethyl-5-hydroxypyrazole | |
| I-2-36 | — | CH$_2$ | O | H | morpholinyl | (2) Cl | (4) Cl | 2-methylcyclohexane-1,3-dione | |
| I-2-37 | — | CH$_2$ | O | H | morpholinyl | (2) Cl | (4) Cl | 1,4-dimethyl-5-hydroxypyrazole | |

TABLE 1-continued
Examples of compounds of the formula (I-2)
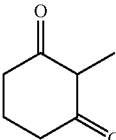
(I-2)
| Ex. No. | $A^1$ | $A^2$ | Q | $R^1$ | $R^2$ | (position) X | (position) Y | Z | Physical data |
|---|---|---|---|---|---|---|---|---|---|
| I-2-38 | — | $CH_2$ | O | $CH_3$ | $NH_2$ | (2) Cl | (4) Cl | 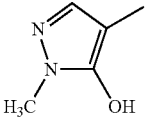 | |
| I-2-39 | — | $CH_2$ | O | $CH_3$ | $NH_2$ | (2) Cl | (4) Cl | 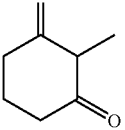 | |
| I-2-40 | — | $CH_2$ | O | H | $NH_2$ | (2) Cl | (4) Cl | 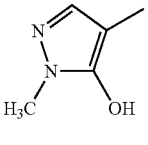 | |
| I-2-41 | — | $CH_2$ | O | H | $NH_2$ | (2) Cl | (4) Cl | 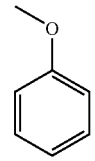 | |
| I-2-42 | — | $CH_2$ | O | $C_3H_7$-i | 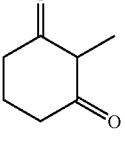 | (2) Cl | (4) Cl | 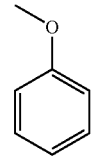 | log P = 4.25[a)] |
| I-2-43 | — | $CH_2$ | O | $C_3H_7$-i | 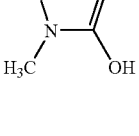 | (2) Cl | (4) Cl | 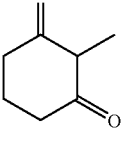 | log P = 3.19[a)] |
| I-2-44 | — | $CH_2$ | O | $C_3H_7$-i | $OC_2H_5$ | (2) Cl | (4) Cl | 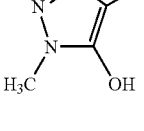 | log P = 3.69[a)] |
| I-2-45 | — | $CH_2$ | O | $C_3H_7$-i | $OC_2H_5$ | (2) Cl | (4) Cl | | log P = 2.69[a)] |

TABLE 1-continued
Examples of compounds of the formula (I-2)
(I-2)
| Ex. No. | A¹ | A² | Q | R¹ | R² | (position) X | (position) Y | Z | Physical data |
|---------|----|----|----|----|----|----|----|----|----|
| I-2-46 | — | CH$_2$ | O | H | OC$_2$H$_5$ | (2) Cl | (4) Cl | 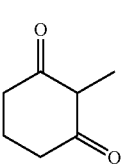 | |
| I-2-47 | — | CH$_2$ | O | H | OC$_2$H$_5$ | (2) Cl | (4) Cl | 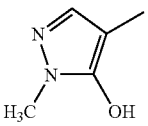 | |
| I-2-48 | — | CH$_2$ | O | H | OC$_3$H$_7$-i | (2) Cl | (4) Cl | 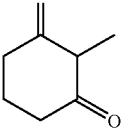 | |
| I-2-49 | — | CH$_2$ | O | H | OC$_3$H$_7$-i | (2) Cl | (4) Cl | 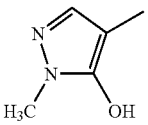 | |
| I-2-50 | — | CH$_2$ | O | CH$_3$ | OC$_2$H$_5$ | (2) Cl | (4) Cl | 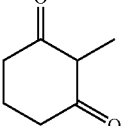 | |
| I-2-51 | — | CH$_2$ | O | CH$_3$ | OC$_2$H$_5$ | (2) Cl | (4) Cl | 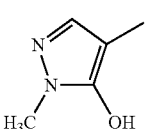 | |
| I-2-52 | — | CH$_2$ | O | H | NHOCH$_3$ | (2) Cl | (4) Cl | 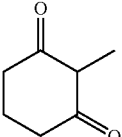 | |
| I-2-53 | — | CH$_2$ | O | H | NHOCH$_3$ | (2) Cl | (4) Cl | 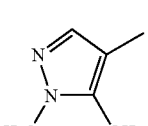 | |

TABLE 1-continued
Examples of compounds of the formula (I-2)
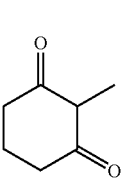
(I-2)
| Ex. No. | A¹ | A² | Q | R¹ | R² | (position) X | (position) Y | Z | Physical data |
|---|---|---|---|---|---|---|---|---|---|
| I-2-54 | — | CH$_2$ | O | H | N(CH$_3$)O—CH$_3$ | (2) Cl | (4) Cl | 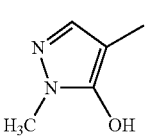 | |
| I-2-55 | — | CH$_2$ | O | H | N(CH$_3$)O—CH$_3$ | (2) Cl | (4) Cl |  | |
| I-2-56 | — | CH$_2$ | O | 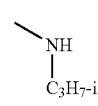 | NH—C$_3$H$_7$-i | (2) Cl | (4) Cl | 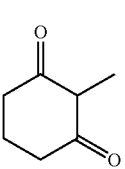 | log P = 2.75[a)] |
| I-2-57 | — | CH$_2$ | O |  | NH—C$_3$H$_7$-i | (2) Cl | (4) Cl | 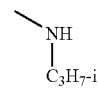 | |
| I-2-58 | — | CH$_2$ | S | C$_3$H$_7$-i | NH—CH$_3$ | (2) Cl | (4) Cl | 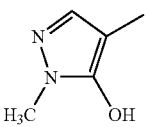 | log P = 1.91[a)] |
| I-2-59 | — | CH$_2$ | O | CH$_3$ | NH—CH$_3$ | (2) Cl | (4) Cl | 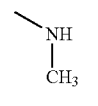 | log P = 1.81[a)] |
| I-2-60 | — | CH$_2$ | O | CH$_3$ | NH—CH$_3$ | (2) Cl | (4) Cl | 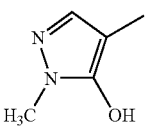 | log P = 1.11[a)] |
| I-2-61 | — | CH$_2$ | O | CH$_3$ | N(CH$_3$)$_2$ | (2) Cl | (4) Cl | 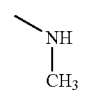 | log P = 2.26[a)] |

TABLE 1-continued

Examples of compounds of the formula (I-2)

(I-2)

| Ex. No. | A¹ | A² | Q | R¹ | R² | (position) X | (position) Y | Z | Physical data |
|---|---|---|---|---|---|---|---|---|---|
| I-2-62 | — | CH₂ | O | CH₃ | N(CH₃)₂ | (2) Cl | (4) Cl | 1-methyl-5-hydroxypyrazol-4-yl | log P = 1.48ᵃ⁾ |
| I-2-63 | — | CH₂ | S | CH₃ | NH-CH₃ | (2) Cl | (4) SO₂CH₃ | 2-methyl-1,3-cyclohexanedione | log P = 1.81ᵃ⁾ |
| I-2-64 | — | CH₂ | S | CH₃ | NH-CH₃ | (2) Cl | (4) SO₂CH₃ | 1-methyl-5-hydroxypyrazol-4-yl | log P = 1.00ᵃ⁾ |
| I-2-65 | — | CH₂ | O | H | NH₂ | (2) Cl | (4) SO₂CH₃ | 1-methyl-5-hydroxypyrazol-4-yl | log P = 0.30ᵃ⁾ |
| I-2-66 | — | CH₂ | O | H | NH-C₂H₅ | (2) Cl | (4) SO₂CH₃ | 2-methyl-1,3-cyclohexanedione | log P = 1.57ᵃ⁾ |
| I-2-67 | O | (CH₂)₂ | O | H | CH₃ | (2) Cl | (4) Cl | 2-methyl-1,3-cyclohexanedione | |
| I-2-68 | O | (CH₂)₂ | O | H | cyclopropyl | (2) Cl | (4) Cl | 2-methyl-1,3-cyclohexanedione | log P = 2.28ᵃ⁾ |
| I-2-69 | O | (CH₂)₂ | O | H | OC₃H₇-i | (2) Cl | (4) Cl | 2-methyl-1,3-cyclohexanedione | log P = 2.98ᵃ⁾ |

TABLE 1-continued

Examples of compounds of the formula (I-2)

(I-2)

| Ex. No. | A¹ | A² | Q | R¹ | R² | (position) X | (position) Y | Z | Physical data |
|---|---|---|---|---|---|---|---|---|---|
| I-2-70 | O | (CH$_2$)$_2$ | O | H | OC$_3$H$_7$-i | (2) Cl | (4) Cl | pyrazole with H$_5$C$_2$, OH | log P = 2.46$^{a)}$ |
| I-2-71 | O | (CH$_2$)$_2$ | O | H | C$_2$H$_5$ | (2) Cl | (4) Cl | methyl cyclohexane-1,3-dione | |
| I-2-72 | O | (CH$_2$)$_2$ | O | H | C$_2$H$_5$ | (2) Cl | (4) Cl | pyrazole with H$_5$C$_2$, OH | log P = 1.64$^{a)}$ |
| I-2-73 | O | (CH$_2$)$_2$ | O | H | NHCH$_3$ | (2) Cl | (4) Cl | methyl cyclohexane-1,3-dione | log P = 1.84$^{a)}$ |
| I-2-74 | O | (CH$_2$)$_2$ | O | H | NHCH$_3$ | (2) Cl | (4) Cl | pyrazole with H$_5$C$_2$, OH | log P = 1.37$^{a)}$ |
| I-2-75 | O | (CH$_2$)$_2$ | S | H | NHCH$_3$ | (2) Cl | (4) Cl | methyl cyclohexane-1,3-dione | log P = 2.23$^{a)}$ |
| I-2-76 | O | (CH$_2$)$_2$ | S | H | NHCH$_3$ | (2) Cl | (4) Cl | pyrazole with H$_5$C$_2$, OH | log P = 1.73$^{a)}$ |
| I-2-77 | O | (CH$_2$)$_2$ | O | H | CF$_3$ | (2) Cl | (4) Cl | methyl cyclohexane-1,3-dione | |

TABLE 1-continued

Examples of compounds of the formula (I-2)

(I-2)

| Ex. No. | A¹ | A² | Q | R¹ | R² | (position) X | (position) Y | Z | Physical data |
|---|---|---|---|---|---|---|---|---|---|
| I-2-78 | O | (CH$_2$)$_2$ | O | H | CF$_3$ | (2) Cl | (4) Cl | 1-ethyl-5-hydroxy-4-methylpyrazole | |
| I-2-79 | — | CH$_2$ | O | H | NH$_2$ | (2) Cl | (4) SO$_2$CH$_3$ | | log P = 1.23$^{a)}$ |
| I-2-80 | — | CH$_2$ | O | H | NH-C$_2$H$_5$ | (2) Cl | (4) SO$_2$CH$_3$ | 1-methyl-5-hydroxy-4-methylpyrazole | log P = 0.74$^{a)}$ |
| I-2-81 | — | CH$_2$ | O | H | NH-(2-methylphenyl) | (2) Cl | (4) SO$_2$CH$_3$ | 1-methyl-5-hydroxy-4-methylpyrazole | log P = 1.58$^{a)}$ |
| I-2-82 | — | CH$_2$ | O | H | N(CH$_3$)$_2$ | (2) Cl | (4) SO$_2$CH$_3$ | 2-methyl-1,3-cyclohexanedione | log P = 1.58$^{a)}$ |
| I-2-83 | — | CH$_2$ | O | H | N(CH$_3$)$_2$ | (2) Cl | (4) SO$_2$CH$_3$ | 1-methyl-5-hydroxy-4-methylpyrazole | log P = 0.77$^{a)}$ |
| I-2-84 | — | CH$_2$ | O | OCH$_3$ | NH-CH$_3$ | (2) Cl | (4) Cl | 2-methyl-1,3-cyclohexanedione | |
| I-2-85 | — | CH$_2$ | O | OCH$_3$ | NH-CH$_3$ | (2) Cl | (4) Cl | 1-methyl-5-hydroxy-4-methylpyrazole | |
| I-2-86 | — | CH$_2$ | O | OCH$_3$ | NH-CH$_3$ | (2) Cl | (4) SO$_2$CH$_3$ | 2-methyl-1,3-cyclohexanedione | |

TABLE 1-continued

Examples of compounds of the formula (I-2)

(I-2)

| Ex. No. | A¹ | A² | Q | R¹ | R² | (position) X | (position) Y | Z | Physical data |
|---|---|---|---|---|---|---|---|---|---|
| I-2-87 | — | CH₂ | O | OCH₃ | NH-CH₃ | (2) Cl | (4) SO₂CH₃ | 1-methyl-4-methyl-5-hydroxypyrazole | |
| I-2-88 | — | CH₂ | O | OCH₃ | NH-C₂H₅ | (2) Cl | (4) Cl | 2-methylcyclohexane-1,3-dione | |
| I-2-89 | — | CH₂ | O | OCH₃ | NH-C₂H₅ | (2) Cl | (4) Cl | 1-methyl-4-methyl-5-hydroxypyrazole | |
| I-2-90 | — | CH₂ | O | OCH₃ | NH-C₂H₅ | (2) Cl | (4) SO₂CH₃ | 2-methylcyclohexane-1,3-dione | |
| I-2-91 | — | CH₂ | O | OCH₃ | NH-C₂H₅ | (2) Cl | (4) SO₂CH₃ | 1-methyl-4-methyl-5-hydroxypyrazole | |
| I-2-92 | — | CH₂ | O | H | N(CH₃)₂ | (2) Cl | (4) SO₂CH₃ | 2-methylcyclohexane-1,3-dione | |
| I-2-93 | — | CH₂ | O | H | N(CH₃)₂ | (2) Cl | (4) SO₂CH₃ | 1-methyl-4-methyl-5-hydroxypyrazole | |
| I-2-94 | — | CH₂ | O | H | NH-C₃H₇-i | (2) Cl | (4) SO₂CH₃ | 2-methylcyclohexane-1,3-dione | |

TABLE 1-continued

Examples of compounds of the formula (I-2)

(I-2)

| Ex. No. | A$^1$ | A$^2$ | Q | R$^1$ | R$^2$ | (position) X | (position) Y | Z | Physical data |
|---|---|---|---|---|---|---|---|---|---|
| I-2-95 | — | CH$_2$ | O | H | NH-C$_3$H$_7$-i | (2) Cl | (4) SO$_2$CH$_3$ | 1-methyl-4-methyl-5-hydroxypyrazol-3-yl | |
| I-2-96 | — | CH$_2$ | O | cyclopropyl | NH-C$_3$H$_7$-i | (2) Cl | (4) SO$_2$CH$_3$ | 2-methyl-1,3-cyclohexanedion-yl | |
| I-2-97 | — | CH$_2$ | O | cyclopropyl | NH-C$_3$H$_7$-i | (2) Cl | (4) SO$_2$CH$_3$ | 1-methyl-4-methyl-5-hydroxypyrazol-3-yl | |
| I-2-98 | — | CH$_2$ | O | cyclopropyl | NHCH$_3$ | (2) Cl | (4) SO$_2$CH$_3$ | 2-methyl-1,3-cyclohexanedion-yl | |
| I-2-99 | — | CH$_2$ | O | cyclopropyl | NHCH$_3$ | (2) Cl | (4) SO$_2$CH$_3$ | 1-methyl-4-methyl-5-hydroxypyrazol-3-yl | |
| I-2-100 | — | CH$_2$ | O | cyclopropyl | NH$_2$ | (2) Cl | (4) SO$_2$CH$_3$ | 2-methyl-1,3-cyclohexanedion-yl | |
| I-2-101 | — | CH$_2$ | O | cyclopropyl | NH$_2$ | (2) Cl | (4) SO$_2$CH$_3$ | 1-methyl-4-methyl-5-hydroxypyrazol-3-yl | |
| I-2-102 | — | CH$_2$ | O | cyclopropyl | N(CH$_3$)$_2$ | (2) Cl | (4) SO$_2$CH$_3$ | 2-methyl-1,3-cyclohexanedion-yl | |

TABLE 1-continued
Examples of compounds of the formula (I-2)
(I-2)
| Ex. No. | A¹ | A² | Q | R¹ | R² | (position) X | (position) Y | Z | Physical data |
|---|---|---|---|---|---|---|---|---|---|
| I-2-103 | — | CH₂ | O | 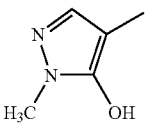 | N(CH₃)₂ | (2) Cl | (4) SO₂CH₃ | 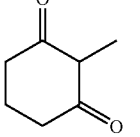 | |
| I-2-104 | — | CH₂ | O | CH₃ | NHC₂H₅ | (2) Cl | (4) SO₂CH₃ | 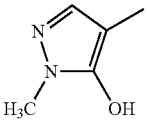 | |
| I-2-105 | — | CH₂ | O | CH₃ | NHCH₃ | (2) Cl | (4) SO₂CH₃ | 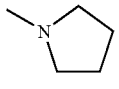 | |
| I-2-106 | — | CH₂ | O | H | 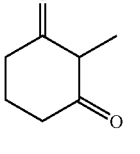 | (2) Cl | (4) SO₂CH₃ | 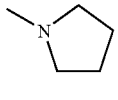 | |
| I-2-107 | — | CH₂ | O | H | 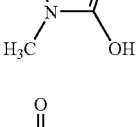 | (2) Cl | (4) SO₂CH₃ | 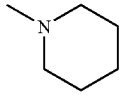 | |
| I-2-108 | — | CH₂ | O | H | 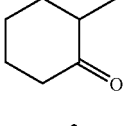 | (2) Cl | (4) SO₂CH₃ | 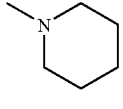 | |
| I-2-109 | — | CH₂ | O | H | 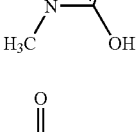 | (2) Cl | (4) SO₂CH₃ | 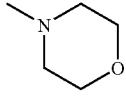 | |
| I-2-110 | — | CH₂ | O | H | 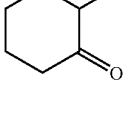 | (2) Cl | (4) SO₂CH₃ | | |

TABLE 1-continued

Examples of compounds of the formula (I-2)

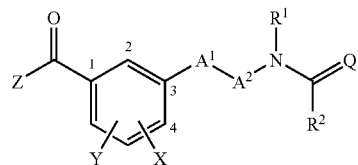

(I-2)

| Ex. No. | A¹ | A² | Q | R¹ | R² | (position) X | (position) Y | Z | Physical data |
|---|---|---|---|---|---|---|---|---|---|
| I-2-111 | — | CH$_2$ | O | H | 4-methylmorpholine | (2) Cl | (4) SO$_2$CH$_3$ | 1-methyl-4-methyl-5-hydroxypyrazole | |
| I-2-112 | — | CH$_2$ | O | phenyl | NHCH$_3$ | (2) Cl | (4) SO$_2$CH$_3$ | 2-methyl-1,3-cyclohexanedione | |
| I-2-113 | — | CH$_2$ | O | phenyl | NHCH$_3$ | (2) Cl | (4) SO$_2$CH$_3$ | 1-methyl-4-methyl-5-hydroxypyrazole | |
| I-2-114 | — | CH$_2$ | O | phenyl | N(CH$_3$)$_2$ | (2) Cl | (4) SO$_2$CH$_3$ | 2-methyl-1,3-cyclohexanedione | |
| I-2-115 | — | CH$_2$ | O | phenyl | N(CH$_3$)$_2$ | (2) Cl | (4) SO$_2$CH$_3$ | 1-methyl-4-methyl-5-hydroxypyrazole | |
| I-2-116 | — | CH$_2$ | O | H | NH$_2$ | (2) Cl | (4) SO$_2$CH$_3$ | 1-methyl-4-methyl-5-hydroxypyrazole | |
| I-2-117 | — | CH$_2$ | O | H | NH$_2$ | (2) Cl | (4) SO$_2$CH$_3$ | 1-methyl-4-methyl-5-hydroxypyrazole | |
| I-2-118 | O | (CH$_2$)$_2$ | O | H | NH$_2$ | (2) Cl | (4) Cl | 1-methyl-4-methyl-5-hydroxypyrazole | log P = 1.66[a] |

TABLE 1-continued

Examples of compounds of the formula (I-2)

(I-2)

| Ex. No. | A¹ | A² | Q | R¹ | R² | (position) X | (position) Y | Z | Physical data |
|---|---|---|---|---|---|---|---|---|---|
| I-2-119 | O | (CH$_2$)$_2$ | O | H | NH$_2$ | (2) Cl | (4) Cl | 1-methyl-5-hydroxy-pyrazol-4-yl | log P = 1.22$^{a)}$ |
| I-2-120 | — | CH$_2$ | O | OCH$_3$ | NH$_2$ | (2) Cl | (4) Cl | 1-methyl-5-hydroxy-pyrazol-4-yl | |
| I-2-121 | — | CH$_2$ | O | OCH$_3$ | NH$_2$ | (2) Cl | (4) Cl | 1-ethyl-5-hydroxy-pyrazol-4-yl | |
| I-2-122 | — | CH$_2$ | O | OCH$_3$ | NH$_2$ | (2) Cl | (4) SO$_2$CH$_3$ | 2-methyl-1,3-cyclohexanedion-2-yl | |
| I-2-123 | — | CH$_2$ | O | OCH$_3$ | NH$_2$ | (2) Cl | (4) SO$_2$CH$_3$ | 1-ethyl-5-hydroxy-pyrazol-4-yl | |
| I-2-124 | — | CH$_2$ | O | OCH$_3$ | NHCH$_3$ | (2) Cl | (4) Cl | 2-methyl-1,3-cyclohexanedion-2-yl | |
| I-2-125 | — | CH$_2$ | O | OCH$_3$ | NHCH$_3$ | (2) Cl | (4) Cl | 1-ethyl-5-hydroxy-pyrazol-4-yl | |
| I-2-126 | — | CH$_2$ | O | OCH$_3$ | NHCH$_3$ | (2) Cl | (4) SO$_2$CH$_3$ | 2-methyl-1,3-cyclohexanedion-2-yl | |

TABLE 1-continued

Examples of compounds of the formula (I-2)

(I-2)

| Ex. No. | A¹ | A² | Q | R¹ | R² | (position) X | (position) Y | Z | Physical data |
|---|---|---|---|---|---|---|---|---|---|
| I-2-127 | — | CH₂ | O | OCH₃ | NHCH₃ | (2) Cl | (4) SO₂CH₃ | 1-ethyl-5-hydroxy-4-methylpyrazole | |
| I-2-128 | — | CH₂ | O | OCH₃ | N(CH₃)₂ | (2) Cl | (4) Cl | 2-methylcyclohexane-1,3-dione | |
| I-2-129 | — | CH₂ | O | OCH₃ | N(CH₃)₂ | (2) Cl | (4) Cl | 1-ethyl-5-hydroxy-4-methylpyrazole | |
| I-2-130 | — | CH₂ | O | OCH₃ | N(CH₃)₂ | (2) Cl | (4) SO₂CH₃ | 2-methylcyclohexane-1,3-dione | |
| I-2-131 | — | CH₂ | O | OCH₃ | N(CH₃)₂ | (2) Cl | (4) SO₂CH₃ | 1-ethyl-5-hydroxy-4-methylpyrazole | |
| I-2-132 | — | CH₂ | O | OCH₃ | NH-cyclopropyl | (2) Cl | (4) Cl | 2-methylcyclohexane-1,3-dione | |
| I-2-133 | — | CH₂ | O | OCH₃ | NH-cyclopropyl | (2) Cl | (4) Cl | 1-ethyl-5-hydroxy-4-methylpyrazole | |
| I-2-134 | — | CH₂ | O | OCH₃ | NH-cyclopropyl | (2) Cl | (4) SO₂CH₃ | 2-methylcyclohexane-1,3-dione | |

TABLE 1-continued
Examples of compounds of the formula (I-2)
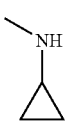
| Ex. No. | A¹ | A² | Q | R¹ | R² | (position) X | (position) Y | Z | Physical data |
|---|---|---|---|---|---|---|---|---|---|
| I-2-135 | — | CH₂ | O | OCH₃ | 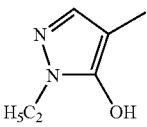 | (2) Cl | (4) SO₂CH₃ | 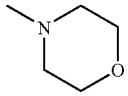 | |
| I-2-136 | — | CH₂ | O | OCH₃ | 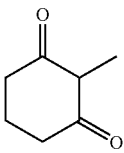 | (2) Cl | (4) Cl | 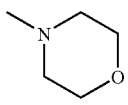 | |
| I-2-137 | — | CH₂ | O | OCH₃ | 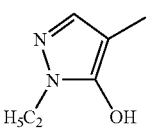 | (2) Cl | (4) Cl | 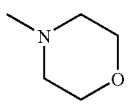 | |
| I-2-138 | — | CH₂ | O | OCH₃ | 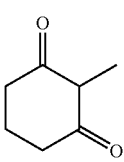 | (2) Cl | (4) SO₂CH₃ | 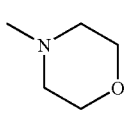 | |
| I-2-139 | — | CH₂ | O | OCH₃ | 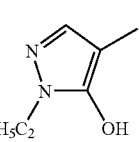 | (2) Cl | (4) SO₂CH₃ | 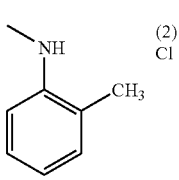 | |
| I-2-140 | — | CH₂ | O | H | 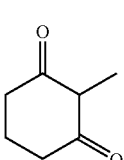 | (2) Cl | (4) SO₂CH₃ | 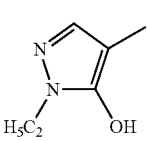 | log P = 2.35[a)] |
| I-2-141 | O | (CH₂)₂ | O | H | CH₃ | (2) Cl | (4) SO₂CH₃ | 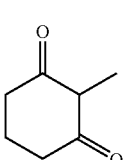 | |
| I-2-142 | O | (CH₂)₂ | O | H | CH₃ | (2) Cl | (4) SO₂CH₃ | | |

TABLE 1-continued

Examples of compounds of the formula (I-2)

(I-2)

| Ex. No. | A¹ | A² | Q | R¹ | R² | (position) X | (position) Y | Z | Physical data |
|---|---|---|---|---|---|---|---|---|---|
| I-2-143 | O | (CH₂)₂ | O | H | C₂H₅ | (2) Cl | (4) SO₂CH₃ | 4-methyl-1-ethyl-5-hydroxypyrazole | |
| I-2-144 | O | (CH₂)₂ | O | H | C₂H₅ | (2) Cl | (4) SO₂CH₃ | 2-methylcyclohexane-1,3-dione | |
| I-2-145 | O | -CH₂-CH(CH₃)- | O | H | CH₃ | (2) Cl | (4) Cl | 4-methyl-1-ethyl-5-hydroxypyrazole | |
| I-2-146 | O | -CH₂-CH(CH₃)- | O | H | CH₃ | (2) Cl | (4) Cl | 2-methylcyclohexane-1,3-dione | |
| I-2-147 | O | -CH₂-CH(CH₃)- | O | H | C₂H₅ | (2) Cl | (4) Cl | 4-methyl-1-ethyl-5-hydroxypyrazole | |
| I-2-148 | O | -CH₂-CH(CH₃)- | O | H | C₂H₅ | (2) Cl | (4) Cl | 2-methylcyclohexane-1,3-dione | |
| I-2-149 | O | -CH₂-CH(CH₃)- | O | H | CH₃ | (2) Cl | (4) SO₂CH₃ | 4-methyl-1-ethyl-5-hydroxypyrazole | |
| I-2-150 | O | -CH₂-CH(CH₃)- | O | H | CH₃ | (2) Cl | (4) SO₂CH₃ | 2-methylcyclohexane-1,3-dione | |

TABLE 1-continued

Examples of compounds of the formula (I-2)

(I-2)

[Structure: benzene ring with substituents — C(=O)Z at position 1, X at position 2, A¹–A²–N(R¹)–C(=O)Q at position 3, with R² on N; Y at position 4]

| Ex. No. | A¹ | A² | Q | R¹ | R² | (position) X | (position) Y | Z | Physical data |
|---|---|---|---|---|---|---|---|---|---|
| I-2-151 | O | –CH₂–CH(CH₃)– | O | H | C₂H₅ | (2) Cl | (4) SO₂CH₃ | [1-ethyl-4-methyl-5-hydroxypyrazol-1-yl] | |
| I-2-152 | O | –CH₂–CH(CH₃)– | O | H | C₂H₅ | (2) Cl | (4) SO₂CH₃ | [2-methyl-1,3-cyclohexanedione-yl] | |

TABLE 2

Examples of compounds of the formula (I-3)

(I-3)

[Structure: benzene ring with C(=O)Z at position 1, X at position 2, position 3, A¹–A²–N(R¹)–C(=O)Q at position 4, Y also on ring; R² on N]

| Ex. No. | A¹ | A² | Q | R¹ | R² | (position) X | (position) Y | Z | Physical data |
|---|---|---|---|---|---|---|---|---|---|
| I-3-1 | — | CH₂ | O | H | NH—NO₂ | (2) NO₂ | — | [1-methyl-5-hydroxypyrazol-1-yl] | m.p.: 191° C. |
| I-3-2 | — | CH₂ | O | CH₃ | NHCH₃ | (2) NO₂ | — | [2-methyl-1,3-cyclohexanedione-yl] | |
| I-3-3 | — | CH₂ | O | C₂H₅ | NHC₂H₅ | (2) NO₂ | — | [2-methyl-1,3-cyclohexanedione-yl] | |

TABLE 2-continued
Examples of compounds of the formula (I-3)
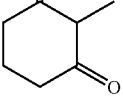
(I-3)
| Ex. No. | A¹ | A² | Q | R¹ | R² | (position) X | (position) Y | Z | Physical data |
|---|---|---|---|---|---|---|---|---|---|
| I-3-4 | — | (CH$_2$)$_2$ | O | H | CH$_3$ | (2) NO$_2$ | — |  | |
| I-3-5 | — | CH$_2$ | O | C$_3$H$_7$-i | 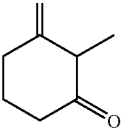 | (2) NO$_2$ | — | 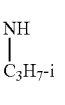 | log P = 2.53[a)] |
| I-3-6 | — | CH$_2$ | O | C$_3$H$_7$-i | 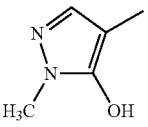 | (2) NO$_2$ | — | 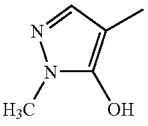 | log P = 1.64[a)] |
| I-3-7 | — | CH$_2$ | O | C$_3$H$_7$-i | N(CH$_3$)$_2$ | (2) NO$_2$ | — | 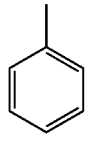 | log P = 1.63[a)] |
| I-3-8 | — | CH$_2$ | O | 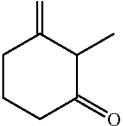 | NHC$_2$H$_5$ | (2) NO$_2$ | — | 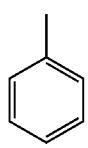 | log P = 2.60[a)] |
| I-3-9 | — | CH$_2$ | O | 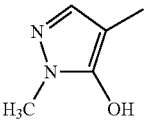 | NHC$_2$H$_5$ | (2) NO$_2$ | — | 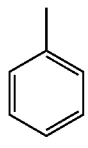 | log P = 1.75[a)] |
| I-3-10 | — | CH$_2$ | O | 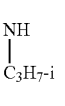 | 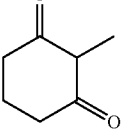 | (2) NO$_2$ | — | 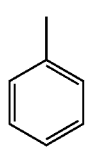 | log P = 2.94[a)] |
| I-3-11 | — | CH$_2$ | O |  | 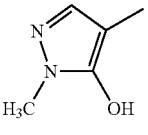 | (2) NO$_2$ | — |  | log P = 2.05[a)] |

TABLE 2-continued
Examples of compounds of the formula (I-3)
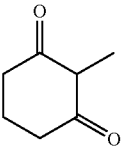
(I-3)
| Ex. No. | A¹ | A² | Q | R¹ | R² | (position) X | (position) Y | Z | Physical data |
|---|---|---|---|---|---|---|---|---|---|
| I-3-12 | — | CH₂ | O | H | N(CH₃)₂ | (2) NO₂ | — | 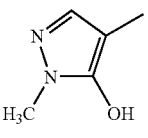 | |
| I-3-13 | — | CH₂ | O | H | N(CH₃)₂ | (2) NO₂ | — |  | |
| I-3-14 | — | CH₂ | O | H | 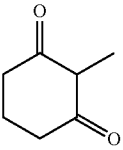 | (2) NO₂ | — |  | |
| I-3-15 | — | CH₂ | O | H | 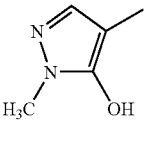 | (2) NO₂ | — |  | |
| I-3-16 | — | CH₂ | O |  | 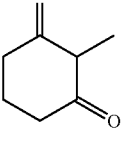 | (2) NO₂ | — |  | |
| I-3-17 | — | CH₂ | O |  | 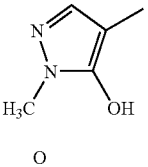 | (2) NO₂ | — |  | |
| I-3-18 | — | CH₂ | O | 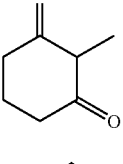 | NHCH₃ | (2) NO₂ | — |  | |
| I-3-19 | — | CH₂ | O | 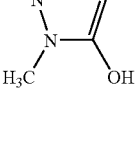 | NHCH₃ | (2) NO₂ | — | | |

TABLE 2-continued

Examples of compounds of the formula (I-3)

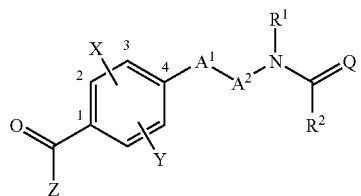

(I-3)

| Ex. No. | A$^1$ | A$^2$ | Q | R$^1$ | R$^2$ | (position) X | (position) Y | Z | Physical data |
|---|---|---|---|---|---|---|---|---|---|
| I-3-20 | — | CH$_2$ | O | cyclopropyl | NH$_2$ | (2) NO$_2$ | — | 2-methyl-cyclohexane-1,3-dione | |
| I-3-21 | — | CH$_2$ | O | cyclopropyl | NH$_2$ | (2) NO$_2$ | — | 1,4-dimethyl-5-hydroxy-pyrazole | |
| I-3-22 | — | CH$_2$ | O | cyclopropyl | N(CH$_3$)$_2$ | (2) NO$_2$ | — | 2-methyl-cyclohexane-1,3-dione | |
| I-3-23 | — | CH$_2$ | O | cyclopropyl | N(CH$_3$)$_2$ | (2) NO$_2$ | — | 1,4-dimethyl-5-hydroxy-pyrazole | |
| I-3-24 | — | CH$_2$ | O | CH$_3$ | NHC$_2$H$_5$ | (2) NO$_2$ | — | 2-methyl-cyclohexane-1,3-dione | |
| I-3-25 | — | CH$_2$ | O | CH$_3$ | NHCH$_3$ | (2) NO$_2$ | — | 1,4-dimethyl-5-hydroxy-pyrazole | log P = 0.68$^{a)}$ |
| I-3-26 | — | CH$_2$ | O | H | pyrrolidin-1-yl | (2) NO$_2$ | — | 2-methyl-cyclohexane-1,3-dione | |
| I-3-27 | — | CH$_2$ | O | H | pyrrolidin-1-yl | (2) NO$_2$ | — | 1,4-dimethyl-5-hydroxy-pyrazole | |

TABLE 2-continued

Examples of compounds of the formula (I-3)

(I-3)

| Ex. No. | A$^1$ | A$^2$ | Q | R$^1$ | R$^2$ | (position) X | (position) Y | Z | Physical data |
|---|---|---|---|---|---|---|---|---|---|
| I-3-28 | — | CH$_2$ | O | H | N-piperidinyl | (2) NO$_2$ | — | 2-methyl-cyclohexane-1,3-dione | |
| I-3-29 | — | CH$_2$ | O | H | N-piperidinyl | (2) NO$_2$ | — | 1,3-dimethyl-5-hydroxypyrazole | |
| I-3-30 | — | CH$_2$ | O | H | N-morpholinyl | (2) NO$_2$ | — | 2-methyl-cyclohexane-1,3-dione | |
| I-3-31 | — | CH$_2$ | O | H | N-morpholinyl | (2) NO$_2$ | — | 1,3-dimethyl-5-hydroxypyrazole | |
| I-3-32 | — | CH$_2$ | O | 4-methylphenyl | NHCH$_3$ | (2) NO$_2$ | — | 2-methyl-cyclohexane-1,3-dione | |
| I-3-33 | — | CH$_2$ | O | 4-methylphenyl | NHCH$_3$ | (2) NO$_2$ | — | 1,3-dimethyl-5-hydroxypyrazole | |
| I-3-34 | — | CH$_2$ | O | 4-methylphenyl | N(CH$_3$)$_2$ | (2) NO$_2$ | — | 2-methyl-cyclohexane-1,3-dione | |
| I-3-35 | — | CH$_2$ | O | 4-methylphenyl | N(CH$_3$)$_2$ | (2) NO$_2$ | — | 1,3-dimethyl-5-hydroxypyrazole | |

TABLE 2-continued

Examples of compounds of the formula (I-3)

(I-3)

| Ex. No. | A¹ | A² | Q | R¹ | R² | (position) X | (position) Y | Z | Physical data |
|---|---|---|---|---|---|---|---|---|---|
| I-3-36 | — | $CH_2$ | O | H | $NH_2$ | (2) $NO_2$ | — | 2-methylcyclohexane-1,3-dione | |
| I-3-37 | — | $CH_2$ | O | H | $NH_2$ | (2) $NO_2$ | — | 1-methyl-4-methyl-5-hydroxypyrazole | |
| I-3-38 | — | $CH_2$ | O | $CH_3$ | $NHC_2H_5$ | (2) $NO_2$ | — | 1-methyl-4-methyl-5-hydroxypyrazole | |
| I-3-39 | — | $CH_2$ | O | $C_3H_7$-i | phenoxymethyl | (2) $NO_2$ | — | 2-methylcyclohexane-1,3-dione | log P = 3.53[a)] |
| I-3-40 | — | $CH_2$ | O | $C_3H_7$-i | phenoxymethyl | (2) $NO_2$ | — | 1-methyl-4-methyl-5-hydroxypyrazole | log P = 2.59[a)] |
| I-3-41 | — | $CH_2$ | O | $C_3H_7$-i | $OC_2H_5$ | (2) $NO_2$ | — | 2-methylcyclohexane-1,3-dione | log P = 3.04[a)] |
| I-3-42 | — | $CH_2$ | O | $C_3H_7$-i | $OC_2H_5$ | (2) $NO_2$ | — | 1-methyl-4-methyl-5-hydroxypyrazole | log P = 2.06[a)] |
| I-3-43 | — | $CH_2$ | O | H | $OC_2H_5$ | (2) $NO_2$ | — | 2-methylcyclohexane-1,3-dione | |

TABLE 2-continued

Examples of compounds of the formula (I-3)

(I-3)

| Ex. No. | A¹ | A² | Q | R¹ | R² | (position) X | (position) Y | Z | Physical data |
|---|---|---|---|---|---|---|---|---|---|
| I-3-44 | — | CH₂ | O | H | OC₂H₅ | (2) NO₂ | — | 1-methyl-4-methyl-5-hydroxypyrazolyl | |
| I-3-45 | — | CH₂ | O | H | OC₃H₇-i | (2) NO₂ | — | 2-methyl-1,3-cyclohexanedionyl | |
| I-3-46 | — | CH₂ | O | H | OC₃H₇-i | (2) NO₂ | — | 1-methyl-4-methyl-5-hydroxypyrazolyl | |
| I-3-47 | — | CH₂ | O | CH₃ | OC₂H₅ | (2) NO₂ | — | 2-methyl-1,3-cyclohexanedionyl | |
| I-3-48 | — | CH₂ | O | CH₃ | OC₂H₅ | (2) NO₂ | — | 1-methyl-4-methyl-5-hydroxypyrazolyl | |
| I-3-49 | — | CH₂ | O | H | NHOCH₃ | (2) NO₂ | — | 2-methyl-1,3-cyclohexanedionyl | |
| I-3-50 | — | CH₂ | O | H | NHOCH₃ | (2) NO₂ | — | 1-methyl-4-methyl-5-hydroxypyrazolyl | |
| I-3-51 | — | CH₂ | O | H | N(CH₃)OCH₃ | (2) NO₂ | — | 2-methyl-1,3-cyclohexanedionyl | |

TABLE 2-continued
Examples of compounds of the formula (I-3)
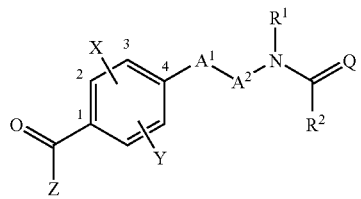
(I-3)
| Ex. No. | $A^1$ | $A^2$ | Q | $R^1$ | $R^2$ | (position) X | (position) Y | Z | Physical data |
|---|---|---|---|---|---|---|---|---|---|
| I-3-52 | — | $CH_2$ | O | H | $N(CH_3)O\\CH_3$ | (2) $NO_2$ | — | 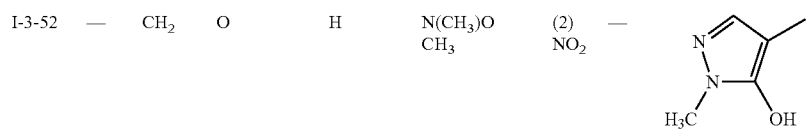 | |
| I-3-53 | — | $CH_2$ | O | $C_3H_7$-i | NH–$C_3H_7$-i | (2) $CF_3$ | — | 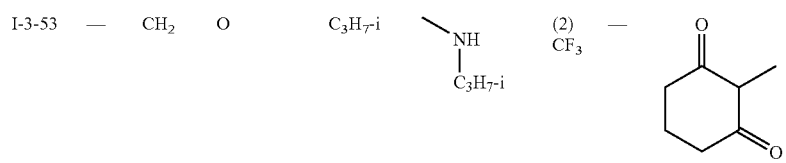 | |
| I-3-54 | — | $CH_2$ | O | $C_3H_7$-i | NH–$C_3H_7$-i | (2) $CF_3$ | — | 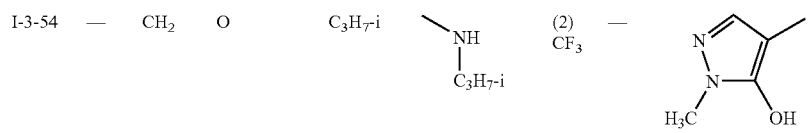 | |
| I-3-55 | — | $CH_2$ | O | $C_3H_7$-i | NH–Ph | (2) $CF_3$ | — | 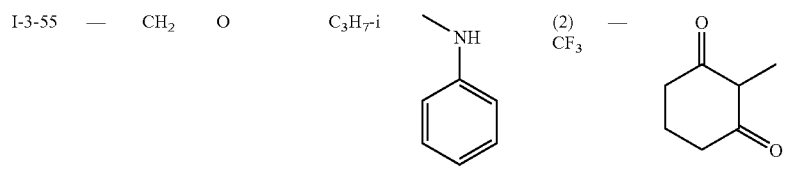 | |
| I-3-56 | — | $CH_2$ | O | $C_3H_7$-i | NH–Ph | (2) $CF_3$ | — | 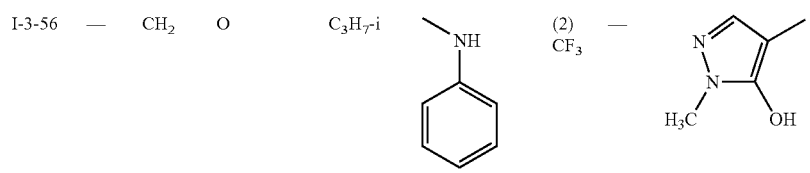 | |
| I-3-57 | — | $CH_2$ | O | H | $N(CH_3)_2$ | (2) $CF_3$ | — | 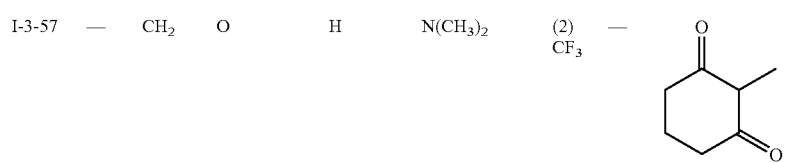 | |
| I-3-58 | — | $CH_2$ | O | H | $N(CH_3)_2$ | (2) $CF_3$ | — | 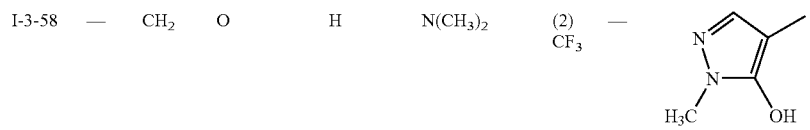 | |

TABLE 2-continued

Examples of compounds of the formula (I-3)

(I-3)

| Ex. No. | A¹ | A² | Q | R¹ | R² | (position) X | (position) Y | Z | Physical data |
|---|---|---|---|---|---|---|---|---|---|
| I-3-59 | — | CH$_2$ | O | H | NH-Ph (N-methyl) | (2) CF$_3$ | — | 2-methylcyclohexane-1,3-dione | |
| I-3-60 | — | CH$_2$ | O | H | NH-Ph (N-methyl) | (2) CF$_3$ | — | 1,4-dimethyl-5-hydroxypyrazole | |
| I-3-61 | — | CH$_2$ | O | H | N(CH$_3$)(i-C$_3$H$_7$) | (2) CF$_3$ | — | 2-methylcyclohexane-1,3-dione | |
| I-3-62 | — | CH$_2$ | O | H | N(CH$_3$)(i-C$_3$H$_7$) | (2) CF$_3$ | — | 1,4-dimethyl-5-hydroxypyrazole | |
| I-3-63 | — | CH$_2$ | O | H | N-morpholinyl | (2) CF$_3$ | — | 2-methylcyclohexane-1,3-dione | |
| I-3-64 | — | CH$_2$ | O | H | N-morpholinyl | (2) CF$_3$ | — | 1,4-dimethyl-5-hydroxypyrazole | |
| I-3-65 | — | CH$_2$ | O | H | N-pyrrolidinyl | (2) CF$_3$ | — | 2-methylcyclohexane-1,3-dione | |
| I-3-66 | — | CH$_2$ | O | H | N-pyrrolidinyl | (2) CF$_3$ | — | 1,4-dimethyl-5-hydroxypyrazole | |

TABLE 2-continued

Examples of compounds of the formula (I-3)

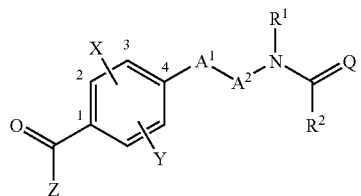

(I-3)

| Ex. No. | A¹ | A² | Q | R¹ | R² | (position) X | (position) Y | Z | Physical data |
|---|---|---|---|---|---|---|---|---|---|
| I-3-67 | — | CH₂ | O | H | N-methylpiperidine | (2) CF₃ | — | 2-methylcyclohexane-1,3-dione | |
| I-3-68 | — | CH₂ | O | H | N-methylpiperidine | (2) CF₃ | — | 1-methyl-5-hydroxy-4-methylpyrazole | |
| I-3-69 | — | CH₂ | O | H | phenoxy | (2) CF₃ | — | 2-methylcyclohexane-1,3-dione | |
| I-3-70 | — | CH₂ | O | H | phenoxy | (2) CF₃ | — | 1-methyl-5-hydroxy-4-methylpyrazole | |
| I-3-71 | — | CH₂ | O | H | OC₂H₅ | (2) CF₃ | — | 2-methylcyclohexane-1,3-dione | |
| I-3-72 | — | CH₂ | O | H | OC₂H₅ | (2) CF₃ | — | 1-methyl-5-hydroxy-4-methylpyrazole | |
| I-3-73 | — | CH₂ | O | C₃H₇-i | phenoxy | (2) CF₃ | — | 2-methylcyclohexane-1,3-dione | |

TABLE 2-continued

Examples of compounds of the formula (I-3)

(I-3)

| Ex. No. | A¹ | A² | Q | R¹ | R² | (position) X | (position) Y | Z | Physical data |
|---|---|---|---|---|---|---|---|---|---|
| I-3-74 | — | CH₂ | O | C₃H₇-i | phenoxy | (2) CF₃ | — | 1-methyl-4-methyl-5-hydroxy-pyrazole | |
| I-3-75 | — | CH₂ | O | C₃H₇-i | OC₂H₅ | (2) CF₃ | — | 2-methyl-cyclohexane-1,3-dione | |
| I-3-76 | — | CH₂ | O | C₃H₇-i | OC₂H₅ | (2) CF₃ | — | 1-methyl-4-methyl-5-hydroxy-pyrazole | |
| I-3-77 | — | CH₂ | O | H | OC₂H₅ | (2) CF₃ | — | 2-methyl-cyclohexane-1,3-dione | |
| I-3-78 | — | CH₂ | O | H | OC₂H₅ | (2) CF₃ | — | 1-methyl-4-methyl-5-hydroxy-pyrazole | |
| I-3-79 | — | CH₂ | O | H | OC₃H₇-i | (2) CF₃ | — | 2-methyl-cyclohexane-1,3-dione | |
| I-3-80 | — | CH₂ | O | H | OC₃H₇-i | (2) CF₃ | — | 1-methyl-4-methyl-5-hydroxy-pyrazole | |
| I-3-81 | — | CH₂ | O | CH₃ | OC₂H₅ | (2) CF₃ | — | 2-methyl-cyclohexane-1,3-dione | |

TABLE 2-continued

Examples of compounds of the formula (I-3)

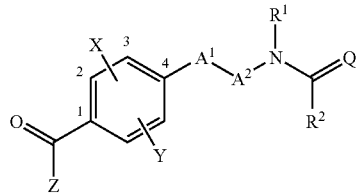

(I-3)

| Ex. No. | A¹ | A² | Q | R¹ | R² | (position) X | (position) Y | Z | Physical data |
|---|---|---|---|---|---|---|---|---|---|
| I-3-82 | — | $CH_2$ | O | $CH_3$ | $OC_2H_5$ | (2) $CF_3$ | — | 1-methyl-5-hydroxy-4-methylpyrazole | |
| I-3-83 | — | $CH_2$ | O | H | $NHOCH_3$ | (2) $CF_3$ | — | 2-methyl-1,3-cyclohexanedione | |
| I-3-84 | — | $CH_2$ | O | H | $NHOCH_3$ | (2) $CF_3$ | — | 1-methyl-5-hydroxy-4-methylpyrazole | |
| I-3-85 | — | $CH_2$ | O | H | $N(CH_3)OCH_3$ | (2) $CF_3$ | — | 2-methyl-1,3-cyclohexanedione | |
| I-3-86 | — | $CH_2$ | O | H | $N(CH_3)OCH_3$ | (2) $CF_3$ | — | 1-methyl-5-hydroxy-4-methylpyrazole | |
| I-3-87 | — | $CH_2$ | O | cyclopropyl | $NHCH_3$ | (2) $CF_3$ | — | 2-methyl-1,3-cyclohexanedione | |
| I-3-88 | — | $CH_2$ | O | cyclopropyl | $NHCH_3$ | (2) $CF_3$ | — | 1-methyl-5-hydroxy-4-methylpyrazole | |
| I-3-89 | — | $CH_2$ | O | cyclopropyl | $N(CH_3)_2$ | (2) $CF_3$ | — | 2-methyl-1,3-cyclohexanedione | |

TABLE 2-continued

Examples of compounds of the formula (I-3)

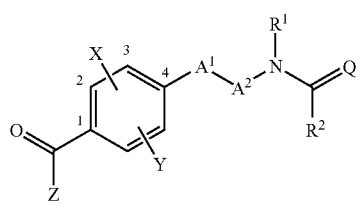
(I-3)

| Ex. No. | A¹ | A² | Q | R¹ | R² | (position) X | (position) Y | Z | Physical data |
|---|---|---|---|---|---|---|---|---|---|
| I-3-90 | — | CH₂ | O | cyclopropyl | N(CH₃)₂ | (2) CF₃ | — | 4-methyl-1-methyl-5-hydroxypyrazole | |
| I-3-91 | — | CH₂ | O | cyclopropyl | OC₂H₅ | (2) CF₃ | — | 2-methyl-1,3-cyclohexanedione | |
| I-3-92 | — | CH₂ | O | cyclopropyl | OC₂H₅ | (2) CF₃ | — | 4-methyl-1-methyl-5-hydroxypyrazole | |
| I-3-93 | — | CH₂ | O | CH₃ | NHCH₃ | (2) CF₃ | — | 2-methyl-1,3-cyclohexanedione | |
| I-3-94 | — | CH₂ | O | CH₃ | NHCH₃ | (2) CF₃ | — | 4-methyl-1-methyl-5-hydroxypyrazole | |
| I-3-95 | — | CH₂ | O | CH₃ | N(CH₃)₂ | (2) CF₃ | — | 2-methyl-1,3-cyclohexanedione | |
| I-3-96 | — | CH₂ | O | CH₃ | N(CH₃)₂ | (2) CF₃ | — | 4-methyl-1-methyl-5-hydroxypyrazole | |

Log P values given in the tables were determined in accordance with EEC Directive 79/831 Annex V.A8 by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding measurement results in Tables 1 and 2 are labelled[a)].

(b) Mobile phases for the determination in the neutral range: 0.01 molar aqueous phosphate buffer solution, acetonitrile; linear gradient from 10% acetonitrile to 90% acetonitrile—the corresponding measurement results in Tables 1 and 2 are labelled[b)].

Calibration was carried out using unbranched alkane-2-ones (having 3 to 16 carbon atoms) with known log P values (determination of the log P values by the retention times using linear interpolation between two successive alkanones).

The lambda max values were determined in the maxima of the chromatographic signals using the UV spectra from 200 nm to 400 nm.

Starting Materials of the Formula (II):

Example (II-1)

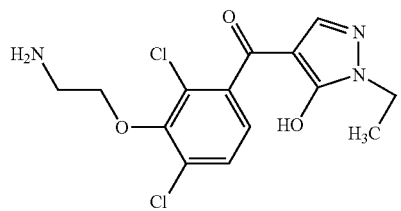

Step 1

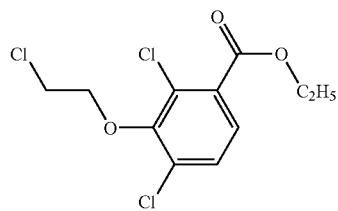

11.7 g (85.1 mmol) of potassium carbonate and, after 15 min, 1.0 g (46.9 mmol) of 2-chloro-ethanol tosylate are added to a solution of 10.0 g (42.5 mmol) of ethyl 2,4-dichloro-3-hydroxy-benzoate in 100 ml of acetonitrile. The reaction mixture is stirred at 70° C. for 19 hours and, after cooling, concentrated under reduced pressure, and 50 ml of water and 50 ml of dichloromethane are added to the residue. The organic phase is separated off, washed with water and saturated aqueous sodium chloride solution, dried over sodium sulphate and filtered. From the filtrate, the solvent is carefully distilled off under reduced pressure.

This gives 12.1 g (95% of theory) of ethyl 2,4-dichloro-3-(2-chloro-ethoxy)-benzoate as an oil.

log P=3.76

Step 2

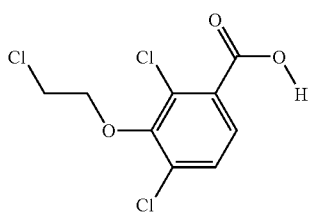

A solution of 2.2 g (55.0 mmol) of sodium hydroxide in 40 ml of water is added to a solution of 10.0 g (33.6 mmol) of ethyl 2,4-dichloro-3-(2-chloro-ethoxy)-benzoate in 70 ml of ethanol. The reaction mixture is stirred at room temperature (about 20° C.) for 90 minutes, and most of the ethanol is removed by evaporation under reduced pressure. The residue is adjusted to pH 1 using conc. hydrochloric acid and extracted with ethyl acetate. The organic phase is separated off, washed with saturated aqueous sodium chloride solution, dried over sodium sulphate and filtered. From the filtrate, the solvent is carefully distilled off under reduced pressure.

This gives 9.0 g (99% of theory) of 2,4-dichloro-3-(2-chloro-ethoxy)-benzoic acid as a white solid.

log P=2.31

Step 3

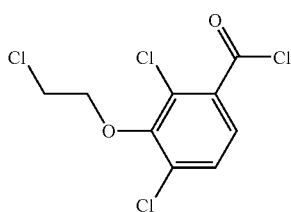

A solution of 8.5 g (31.5 mmol) of 2,4-dichloro-3-(2-chloro-ethoxy)-benzoic acid in 12 ml of thionyl chloride is heated at 60° C. for 1 hour. After the evolution of gas has ceased, the excess thionyl chloride is removed under reduced pressure.

This gives 9.0 g (99% of theory) of 2,4-dichloro-3-(2-chloro-ethoxy)-benzoyl chloride as an oily residue.

Step 4

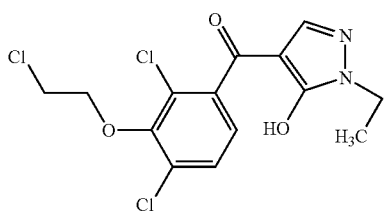

9.5 g of (94 mmol) of triethylamine, 9 g (31.3 mmol) of 2,4-dichloro-3-(2-chloroethoxy)-benzoyl chloride and 5 drops of N,N-dimethylformamide are added successively to a solution of 3.5 g (31.3 mmol) of 1-ethyl-5-hydroxy-1H-pyrazole in 200 ml of dichloromethane. The reaction mixture is stirred at room temperature (about 20° C.), for 21 hours and then washed with 2N hydrochloric acid and saturated aqueous sodium chloride solution, dried over sodium sulphate and filtered. From the filtrate, the solvent is removed under reduced pressure.

The oily residue is dissolved in 200 ml of acetonitrile, 17 g (168 mmol) of triethylamine and 3.26 g (38 mmol) of 2-hydroxy-2-methyl-propionitrile are added and the mixture is stirred at room temperature for another 20 hours. Most of the solvent is then removed under reduced pressure and the oily residue is taken up in 100 ml of dichloromethane. The organic phase is washed with 2N hydrochloric acid and with saturated aqueous sodium chloride solution, dried over sodium sulphate and filtered. The filtrate is freed from the solvent under reduced pressure.

This gives 11.1 g (98% of theory) of [2,4-dichloro-3-(2-chloro-ethoxy)-phenyl]-(1-ethyl-5-hydroxy-1H-pyrazol-4-yl)-methanone as an orange-yellow crystalline solid.

log P=2.73.

Step 5

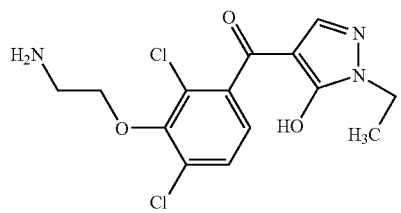

A solution of 8.0 g (22 mmol) of [2,4-dichloro-3-(2-chloro-ethoxy)-phenyl]-(1-ethyl-5-hydroxy-1H-pyrazol-4-yl)-methanone in 150 ml of tetrahydrofuran and 200 ml of ammonia is heated in an autoclave at 90° C. for 6.5 hours. Most of the excess ammonia is evaporated off and the product that settles out is removed by filtration and dried under reduced pressure.

This gives 4.3 g (57% of theory) of [3-(2-amino-ethoxy)-2,4-dichloro-phenyl]-(1-ethyl-5-hydroxy-1H-pyrazol-4-yl)-methanone as a light-yellow crystalline solid.

log P=0.72.

Analogously to Example (II-1), it was also possible to prepare, for example, the compounds of the general formula (II) listed in Table 3 below.

TABLE 3

Examples of compounds of the formula (II)

| Ex. No. | (position) —A¹—A²—NHR¹ | (position) X | (position) Y | Z |
|---|---|---|---|---|
| II-2 | (3) CH₃O-CH₂CH₂-NH-CH₃ | (2) Cl | (4) Cl | pyrazole with N-CH₃, OH |
| II-3 | (3) CH₃O-CH₂CH₂-NH₂ | (2) Cl | (4) SO₂CH₃ | pyrazole with N-CH₃, OH |
| II-4 | (3) CH₃O-CH₂CH₂-NH₂ | (2) Cl | (4) Cl | 2-methyl-cyclohexane-1,3-dione |
| II-5 | (3) CH₃O-CH₂CH₂-NH₂ | (2) Cl | (4) SO₂CH₃ | 2-methyl-cyclohexane-1,3-dione |
| II-6 | (3) CH₃O-CH₂CH₂-N(CH₃)H | (2) Cl | (4) Cl | 2-methyl-cyclohexane-1,3-dione |
| II-7 | (3) CH₃O-CH₂CH₂-N(CH₃)H | (2) Cl | (4) SO₂CH₃ | pyrazole with N-C₂H₅, OH |
| II-8 | (3) CH₃O-CH₂CH₂-N(C₂H₅)H | (2) Cl | (4) Cl | pyrazole with N-CH₃, OH |

Starting Materials of the Formula (IV):

Example (IV-1)

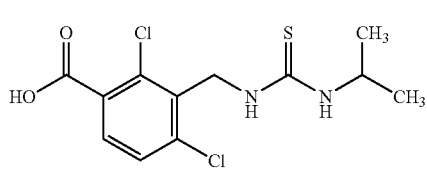

Step 1

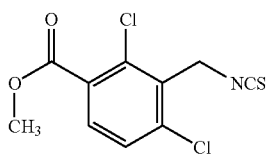

At room temperature (about 20° C.) 15 g (59 mmol) of methyl 2,4-dichloro-3-bromomethyl-benzoate and then 7.5 g (77 mmol) of potassium thiocyanate are introduced into 60 ml of acetonitrile. The reaction mixture is slowly heated to reflux and then stirred at this temperature under reflux for 20 hours. After cooling to room temperature, the solvent is stripped off under reduced pressure and the residue is stirred with 70 ml of diethyl ether. Undissolved components are filtered off with suction, the solvent is removed under reduced pressure and the residue is distilled under reduced pressure.

This gives 2.7 g (17% of theory) of methyl 2,4-dichloro-3-isocyanatomethyl-benzoate as an oil which is reacted further without further purification.

Step 2

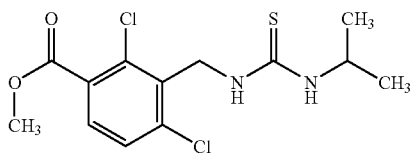

5.6 g of crude methyl 2,4-dichloro-3-isocyanatomethyl-benzoate are dissolved in 20 ml of ethanol, and 1.2 g (20 mmol) of 2-propanamine are added. The mixture is heated at the boil for 1 hour, the amount of solvent is reduced to one third of the original volume and the product is filtered off with suction.

This gives 1.7 g (9%, based on methyl 2,4-dichloro-3-methyl-benzoate) of methyl 2,4-dichloro-3-[[[(isopropylamino)-thioxomethyl]-amino]-methyl]-benzoate as a solid (MS: M⁺=355, 2 Cl according to the isotope pattern).

Step 3

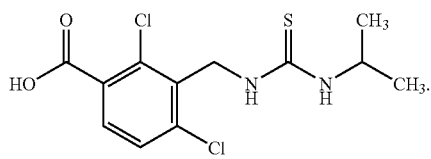

5 g (15 mmol) of N-(3-methoxycarbonyl-2,6-dichloro-benzyl)-N'-isopropyl-thiourea are dissolved in 30 ml of methanol, and 10 ml (50 mmol) of a 30% strength solution of sodium methoxide in methanol are added. Over a period of 30 minutes, 50 ml of water are added dropwise, and the mixture is then kept at 60° C. for 2 hours. Following neutralization with 2N hydrochloric acid, the product is filtered off with suction and dried.

This gives 4.4 g (91% of theory) of 2,4-dichloro-3-[[[(isopropylamino)-thioxomethyl]-amino]-methyl]-benzoic acid as a solid of melting point>220° C.

Analogously to Example (IV-1), it is also possible to prepare, for example, the compounds of the general formula (IVa) listed in Table 4 below.

TABLE 4

Examples of compounds of the formula (IVa)

(IVa)

| Ex. No. | (position) $A^1$-$A^2$-N(R$^1$)-C(R$^2$)(=Q) | (position) X | (position) Y | R | Physical Data |
|---|---|---|---|---|---|
| IV-2 | (3) [structure with HN-C₃H₇-i, H₂C, N-C₃H₇-i, =O] | (2) Cl | (4) Cl | CH₃ | log P = 0.89[a)] |

TABLE 4-continued

Examples of compounds of the formula (IVa)

(IVa)

| Ex. No. | (position) R¹ | (position) X | (position) Y | R | Physical Data |
|---|---|---|---|---|---|
| IV-3 | (3) ethyl-isopropyl-N-C(O)-NH₂ | (2) Cl | (4) Cl | $CH_3$ | m.p.: 195° C. |
| IV-4 | (3) ethyl-isopropyl-N-C(O)-NH-(2-F-phenyl) | (2) Cl | (4) Cl | $CH_3$ | m.p.: 140° C. |
| IV-5 | (3) ethyl-isopropyl-N-C(O)-NH-(2-F-phenyl) | (2) Cl | (4) Cl | H | m.p.: 175° C. |
| IV-6 | (3) ethyl-isopropyl-N-C(O)-NH-(2-methyl-phenyl) | (2) Cl | (4) Cl | $CH_3$ | m.p.: 81° C. |
| IV-7 | (4) ethyl-isopropyl-N-C(O)-NH-C₂H₅ | (2) $NO_2$ | — | $CH_3$ | $n_D^{20} = 1.5361$ |

TABLE 4-continued

Examples of compounds of the formula (IVa)

| Ex. No. | (position) R¹ | (position) X | (position) Y | R | Physical Data |
|---|---|---|---|---|---|
| IV-8 | (3) N,N-di-isopropyl urea ethyl | (2) Cl | (4) Cl | H | m.p. >260° C. |
| IV-9 | (3) N,N-di-isopropyl urea ethyl | (2) Cl | (4) Cl | CH₃ | m.p.: 76° C. |
| IV-10 | (3) N-nitro urea ethyl | (2) NO₂ | — | H | m.p.: >220° C. |
| IV-11 | (4) N-ethyl-N'-isopropyl urea ethyl | (2) NO₂ | — | H | m.p.: 210° C. |
| IV-12 | (3) N-phenyl thiourea ethyl | (2) Cl | (4) Cl | CH₃ | m.p.: 147° C. |
| IV-13 | (3) N-phenyl thiourea ethyl | (2) Cl | (4) Cl | H | m.p.: 173° C. |

USE EXAMPLES

Example A

Pre-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 litres of water per hectare.

After three weeks, the degree of damage to the plants is rated in % damage in comparison to the development of the untreated control. The figures denote:

0%=no effect (like untreated control)

100%=total destruction

In this test, for example, the compounds of Preparation Examples (I-2-1), (I-2-3), (I-2-5) and (I-2-6) exhibit strong activity against weeds, and some are tolerated well by crop plants, such as, for example, maize, soya beans and wheat.

Example B

Post-Emergence Test

Solvent: 5 part by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control. The figures denote:

0%=no effect (like untreated control)

100%=total destruction

In this test, for example, the compounds of Preparation Examples (I-2-1), (I-2-3), (I-2-4), (I-2-5), (I-2-6), (I-2-7) and (I-2-8) exhibit strong activity against weeds, and some are tolerated well by crop plants, such as, for example, maize, oilseed rape and wheat.

The invention claimed is:

1. A compound of the Formula (I)

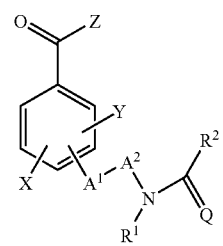

(I)

in which $A^1$ represents a single bond or represents O, S, SO, $SO_2$, $A^2$ represents alkanediyl (alkylene), alkenediyl or alkinediyl, Q represents O (oxygen) or S (sulphur), $R^1$ represents hydrogen or represents in each case optionally substituted alkyl, alkoxy, alkylthio, alkylsulphinyl, alkylsulphonyl, alkylamino, dialkylamino, alkenyl, alkinyl, cycloalkyl, cycloalkylalkyl, aryl or arylalkyl, or represents the grouping —C(Q)-$R^2$, $R^2$ represents hydrogen, amino, cyanoamino, nitroamino, hydroxyamino, hydrazino, or represents in each case optionally substituted alkyl, alkylcarbonyl, alkoxy, alkoxycarbonyl, alkylthio, alkylamino, dialkylamino, alkoxyamino, N-alkyl-alkoxyamino, alkylhydrazino, dialkylhydrazino, alkenyl, alkenyloxy, alkenylamino, alkenyloxyamino, alkinyl, alkinyloxy, alkinylamino, cycloalkyl, cycloalkyloxy, cycloalkylamino, cycloalkylalkyl, cycloalkylalkoxy, cycloalkylalkylamino, aryl, arylcarbonyl, aryloxy, aryloxycarbonyl, arylthio, arylamino, arylhydrazino, arylalkyl, arylalkoxy, arylalkylthio, arylalkylamino, heterocyclyl, heterocyclyloxy, heterocyclylthio, heterocyclylamino, heterocyclylalkyl, heterocyclylalkoxy, heterocyclylalkylthio or heterocyclylalkylamino, X represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, Y represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, and Z represents one of the groupings below

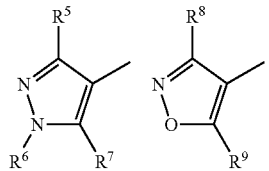

where m represents the numbers 0 to 6, $R^3$ represents hydrogen, halogen or represents in each case optionally substituted alkyl, alkylthio or aryl, or—if m represents 2—optionally also together with a second radical $R^3$ represents oxygen or alkanediyl (alkylene), R⁴ represents hydroxyl, formyloxy, halogen, or represents in each case optionally substituted alkoxy, alkylthio, alkylsulphinyl, alkylsulphonyl, alkylcarbonyloxy, alkoxycarbonyloxy, alkylaminocarbonyloxy, alkylsulphonyloxy, alkenyloxy, alkinyloxy, aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl or arylalkylsulphonyl, R⁵ represents hydrogen, cyano, carbamoyl, thiocarbamoyl, halogen, or represents in each case optionally substituted alkyl, alkoxy, alkylthio, alkylsulphinyl, alkylsulphonyl, alkoxycarbonyl or cycloalkyl, R⁶ represents hydrogen or represents in each case optionally substituted alkyl, alkenyl, alkinyl, cycloalkyl, cycloalkylalkyl, aryl or arylalkyl, R⁷ represents hydroxyl, formyloxy, or represents in each case optionally substituted alkoxy, alkylcarbonyloxy, alkoxycarbonyloxy, alkylaminocarbonyloxy, alkylsulphonyloxy, alkenyloxy, alkinyloxy, arylalkoxy, arylcarbonyloxy, arylcarbonylalkoxy or arylsulphonyloxy, R⁸ represents hydrogen, cyano, carbamoyl, thiocarbamoyl, halogen, or represents in each case optionally substituted alkyl, alkylcarbonyl, alkoxy, alkoxycarbonyl, alkylthio, alkylsulphinyl or alkylsulphonyl, R⁹ represents hydrogen or represents in each case optionally substituted alkyl or cycloalkyl, R¹⁰ represents hydrogen or represents in each case optionally substituted alkyl or cycloalkyl, and R¹¹ represents hydrogen, cyano, carbamoyl, halogen, or represents in each case optionally substituted alkyl, alkoxy, alkoxycarbonyl, alkylthio, alkylsulphinyl or alkylsulphonyl with the proviso that when Q is oxygen, R² is not cyclopropyl and Z is not

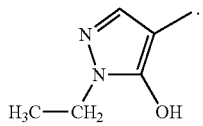

2. A compound of the Formula (I) according to claim 1, wherein

A¹ represents O or represents a single bond,

A² represents alkanediyl (alkylene), alkenediyl or alkinediyl having in each case up to 6 carbon atoms, Q represents O (oxygen), R¹ represents hydrogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl or alkylamino having in each case 1 to 6 carbon atoms in the alkyl groups, represents dialkylamino having in each case 1 to 4 carbon atoms in the alkyl groups, represents in each case optionally cyano- or halogen-substituted alkenyl or alkinyl having in each case 2 to 6 carbon atoms, represents in each case optionally cyano-, halogen- or $C_1$-$C_4$-alkyl-substituted cycloalkyl or cycloalkylalkyl having in each case 3 to 6 carbon atoms in the cycloalkyl group and optionally 1 to 4 carbon atoms in the alkyl moiety, represents in each case optionally nitro-, cyano-, halogen-, $C_1$-$C_4$-alkyl-, $C_1$-$C_4$-halogenoalkyl-, $C_1$-$C_4$-alkoxy- or $C_1$-$C_4$-halogenoalkoxy-substituted aryl or arylalkyl having in each case 6 or 10 carbon atoms in the aryl group and optionally 1 to 4 carbon atoms in the alkyl moiety, or represents the grouping —C(Q)-R², R² represents hydrogen, amino, cyanoamino, nitroamino, hydroxyamino, hydrazino, represents $C_1$-$C_4$-alkyl-carbonyl, represents $C_1$-$C_4$-alkoxycarbonyl, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylamino, alkoxyamino or alkylhydrazino having in each case 1 to 6 carbon atoms in the alkyl groups, represents dialkylamino, N-alkyl-alkoxyamino or dialkylhydrazino having in each case 1 to 4 carbon atoms in the alkyl groups, represents in each case optionally halogen-substituted alkenyl, alkenyloxy, alkenylamino, alkenyloxyamino, alkinyl, alkinyloxy or alkinylamino having in each case 2 to 6 carbon atoms, represents in each case optionally cyano-, halogen- or $C_1$-$C_4$-alkyl-substituted cycloalkyl, cycloalkyloxy, cycloalkylamino, cycloalkylalkyl, cycloalkylalkoxy or cycloalkylalkylamino having in each case 3 to 6 carbon atoms in the cycloalkyl group and optionally 1 to 4 carbon atoms in the alkyl moiety, represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy- or $C_1$-$C_4$-alkoxy-carbonyl-substituted aryl, arylcarbonyl, aryloxy, aryloxycarbonyl, arylthio, arylamino, arylhydrazino, arylalkyl, arylalkoxy, arylalkylthio or arylalkylamino having in each case 6 or 10 carbon atoms in the aryl group and optionally 1 to 4 carbon atoms in the alkyl moiety, or represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-alkylthio-, $C_1$-$C_4$-halogenoalkylthio- or $C_1$-$C_4$-alkoxy-carbonyl-substituted monocyclic or bicyclic heterocyclyl, heterocyclyloxy, heterocyclylthio, heterocyclylamino, heterocyclylalkyl, heterocyclylalkoxy, heterocyclylalkylthio or heterocyclylalkylamino, where in each case the heterocyclyl grouping contains up to 10 carbon atoms and additionally at least one heteroatom selected from the group consisting of nitrogen (N) (but at most 5 N atoms), oxygen (O) (but at most 2 O atoms), sulphur (S) (but at most 2 S atoms), SO and $SO_2$ and also optionally additionally one group selected from the group consisting of oxo (C=O), thioxo (C=S), imino (C=NH), cyanoimino (C=N—CN) and nitroimino (C=N—$NO_2$), X represents hydrogen, nitro, cyano, carboxyl, carbamoyl, thiocarbamoyl, halogen, or represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups, Y represents hydrogen, nitro, cyano, carboxyl, carbamoyl, thiocarbamoyl, halogen, or represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups, Z represents one of the groupings below,

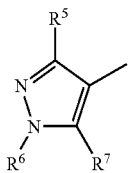

where m represents the numbers 0 to 3, $R^3$ represents hydrogen, halogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl or alkylthio having in each case 1 to 6 carbon atoms, or represents phenyl, or if m represents 2—optionally also together with a second radical $R^3$ represents oxygen or alkanediyl (alkylene) having 3 to 5 carbon atoms, $R^4$ represents hydroxyl, formyloxy, halogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkoxy, alkylthio, alkylsulphinyl, alkylsulphonyl, alkylcarbonyloxy, alkoxycarbonyloxy, alkylaminocarbonyloxy or alkylsulphonyloxy having in each case 1 to 6 carbon atoms, represents in each case optionally halogen-substituted alkenyloxy or alkinyloxy having in each case 3 to 6 carbon atoms, represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkylsulphinyl-, $C_1$-$C_4$-halogenoalkylsulphinyl-, $C_1$-$C_4$-alkylsulphonyl- or $C_1$-$C_4$-halogenoalkylsulphonyl-substituted aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl or arylalkylsulphonyl having in each case 6 or 10 carbon atoms in the aryl group and optionally 1 to 4 carbon atoms in the alkyl moiety, $R^5$ represents hydrogen, cyano, carbamoyl, thiocarbamoyl, halogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl or alkoxycarbonyl having in each case 1 to 6 carbon atoms in the alkyl groups or represents optionally cyano-, halogen- or $C_1$-$C_4$-alkyl-substituted cycloalkyl having 3 to 6 carbon atoms, $R^6$ represents hydrogen, represents optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl having 1 to 6 carbon atoms, represents in each case optionally cyano- or halogen-substituted alkenyl or alkinyl having in each case 3 to 6 carbon atoms, represents in each case optionally cyano-, halogen- or $C_1$-$C_4$-alkyl-substituted cycloalkyl or cycloalkylalkyl having in each case 3 to 6 carbon atoms in the cycloalkyl group and optionally 1 to 4 carbon atoms in the alkyl moiety, or represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-halogenoalkylthio-, $C_1$-$C_4$-alkylsulphinyl-, $C_1$-$C_4$-halogenoalkylsulphinyl-, $C_1$-$C_4$-alkylsulphonyl- or $C_1$-$C_4$-halogenoalkylsulphonyl-substituted aryl or arylalkyl having in each case 6 or 10 carbon atoms in the aryl group and optionally 1 to 4 carbon atoms in the alkyl moiety, $R^7$ represents hydroxyl, formyloxy, represents in each case optionally cyano-, halogen- or $C_1$-$C_4$-alkoxy-substituted alkoxy, alkylcarbonyloxy, alkoxycarbonyloxy, alkylaminocarbonyloxy or alkylsulphonyloxy having in each case 1 to 6 carbon atoms in the alkyl groups, represents in each case optionally cyano-, or halogen-substituted alkenyloxy or alkinyloxy having in each case 3 to 6 carbon atoms, or represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkylsulphinyl-, $C_1$-$C_4$-halogenoalkylsulphinyl-, $C_1$-$C_4$-alkylsulphonyl- or $C_1$-$C_4$-halogenoalkylsulphonyl-substituted arylalkoxy, arylcarbonyloxy, arylcarbonylalkoxy or arylsulphonyloxy having in each case 6 or 10 carbon atoms in the aryl group and optionally 1 to 4 carbon atoms in the alkyl moiety, $R^8$ represents hydrogen, cyano, carbamoyl, thiocarbamoyl, halogen, or represents in each case optionally cyano-, halogen- or $C_1$-$C_4$-alkoxy-substituted alkyl, alkylcarbonyl, alkoxy, alkoxycarbonyl, alkylthio, alkylsulphinyl or alkylsulphonyl having in each case 1 to 6 carbon atoms in the alkyl groups, $R^9$ represents hydrogen, represents optionally cyano-, halogen- or $C_1$-$C_4$-alkoxy-substituted alkyl, or represents optionally cyano-, halogen- or $C_1$-$C_4$-alkyl-substituted cycloalkyl having 3 to 6 carbon atoms, $R^{10}$ represents hydrogen, represents optionally cyano-, halogen- or $C_1$-$C_4$-alkoxy-substituted alkyl, or represents optionally cyano-, halogen- or $C_1$-$C_4$-alkyl-substituted cycloalkyl having 3 to 6 carbon atoms, and $R^{11}$ represents hydrogen, cyano, carbamoyl, halogen, or represents in each case optionally cyano-, halogen- or $C_1$-$C_4$-alkoxy-substituted alkyl, alkoxy, alkoxycarbonyl, alkylthio, alkylsulphinyl or alkylsulphonyl having in each case 1 to 6 carbon atoms in the alkyl groups with the proviso that when Q is oxygen, $R^2$ is not cyclopropyl and Z is not

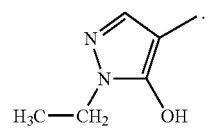

3. A compound of the Formula (1) according to claim 1, wherein $A^2$ represents methylene (—$CH_2$—), ethane-1,1-diyl (—CH($CH_3$)—), ethane-1,2-diyl (dimethylene, —$CH_2CH_2$—), propane-1,1-diyl (—CH($C_2H_5$)—), propane-1,2-diyl (—CH($CH_3$)$CH_2$—), propane-1,3-diyl (—$CH_2CH_2CH_2$—), butane-1,3-diyl (—CH($CH_3$)$CH_2CH_2$—), butane-1,4-diyl (—$CH_2CH_2CH_2CH_2$—), ethenediyl, propenediyl, butenediyl, ethinediyl, propinediyl or butinediyl, $R^1$ represents hydrogen, represents in each case optionally cyano-, fluorine-, chlorine-, bromine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, methylamino, ethylamino, n- or i-propylamino, n-, i-, s- or t-butylamino, represents dimethylamino or diethylamino, represents in each case optionally fluorine-, chlorine- and/or bromine-substituted ethenyl, propenyl, butenyl, pentenyl, ethinyl, propinyl, butinyl or pentinyl, represents in each case optionally cyano-, fluorine-, chlorine-, bromine-, methyl-, ethyl- or propyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, naphthyl, phenylmethyl, phenylethyl, naphthylmethyl or naphthylethyl or represents the grouping —C(Q)-$R^2$, $R^2$ represents hydrogen, amino, cyanoamino, nitroamino, hydroxyamino, hydrazino, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, methoxyamino, ethoxyamino, n- or i-propoxyamino, n-, i-, s- or t-butoxyamino, methylhydrazino, ethylhydrazino, n- or i-propylhydrazino, n-, i-, s- or t-butylhydrazino, represents dimethylamino, diethylamino, N-methylmethoxyamino, dimethylhydrazino or diethylhydrazino, represents in each case optionally fluorine-, chlorine- and/or bromine-substituted ethenyl, propenyl, butenyl, pentenyl, ethinyl, propinyl, butinyl, pentinyl, propenyloxy, butenyloxy, pentenyloxy, propenylthio, butenylthio, pentenylthio, propenylamino, butenylamino, pentenylamino, propenyloxyamino, butenyloxyamino, pentenyloxyamino, ethinyl, propinyl, butinyl, pentinyl, propinyloxy, butinyloxy, pentinyloxy, propinylamino, butinylamino or pentinylamino, represents in each case optionally cyano-, fluorine-, chlorine-, bromine-, methyl-, ethyl- or propyl-substituted cyclopropyl, cyclobutyl, cyclopentyl, cyclohexyl, cyclopropyloxy, cyclobutyloxy, cyclopentyloxy, cyclohexyloxy, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylamino, cyclobutylmethylamino, cyclopentylmethylamino or cyclohexylmethylamino, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, phenylcarbonyl, phenoxy, phenoxycarbonyl, phenylthio, phenylamino, phenylhydrazino, naphthyl, naphthyloxy, naphthylthio, naphthylamino, phenylmethyl, phenylethyl, phenylmethoxy, phenylethoxy, phenylmethylthio, phenylethylthio, phenylmethylamino, phenylethylamino, naphthylmethyl, naphthylethyl, naphthylmethoxy, naphthylethoxy, naphthylmethylamino or naphthylethylamino, or represents in each case optionally nitro-, cyano-, fluorine-, chlorine-, bromine-, methyl-, ethyl-, n- or i-propyl-, n-, i-, s- or t-butyl-, difluoromethyl-, trifluoromethyl-, dichloromethyl-, trichloromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methoxycarbonyl-, ethoxycarbonyl-, n- or i-propoxycarbonyl-substituted monocyclic or bicyclic heterocyclyl, heterocyclyloxy, heterocyclylamino, heterocyclylalkyl, heterocyclylalkoxy or heterocyclylalkylamino from the group consisting of furyl, furyloxy, furylamino, furylmethyl, furylmethoxy, furylmethylamino, thienyl, thienylmethyl, pyrrolidinyl, pyrrolidinylamino, oxopyrrolidinyl, pyrrolyl, indolyl, pyrrolylmethyl, pyrazolyl, pyrazolyloxy, pyrazolylamino, pyrazolylmethyl, imidazolyl, imidazolylmethyl, 2-oxo-1,3-diaza-cyclopentyl, oxazolyl, dihydrooxazolyl (oxazolinyl), isoxazolyl, dihydroisoxazolyl (isoxazolinyl), tetrahydroisoxazolyl (isoxazolidinyl), oxazolylmethyl, thiazolyl, dihydrothiazolyl (thiazolinyl), tetrahydrothiazolyl (thiazolidinyl), thiazolylmethyl, thiazolidinyl, oxothiazolidinyl, cyanoiminothiazolidinyl, oxotriazolinyl, oxotetrazolinyl, piperidinyl, piperidinylamino, oxopiperidinyl, 2-oxo-1,3-diaza-cyclohexyl, 2-oxo-1-aza-cycloheptyl, 2-oxo-1,3-diaza-cycloheptyl, morpholinyl, morpholinylamino, piperazinyl, pyridinyl, pyridinyloxy, pyridinylamino, pyridinylmethyl, pyridinylmethoxy, pyrimidinyl, pyrimidinyloxy, pyrimidinylmethyl, pyrimidinylmethoxy, X represents hydrogen, nitro, cyano, carboxyl, carbamoyl, thiocarbamoyl, fluorine, chlorine, bromine, iodine, or represents in each case optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl, Y represents hydrogen, nitro, cyano, carboxyl, carbamoyl, thiocarbamoyl, fluorine, chlorine, bromine, iodine, or represents in each case optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl m represents the number 0, 1 or 2, $R^3$ represents fluorine, chlorine or bromine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methylthio, ethylthio, n- or i-propylthio, n-, i-, s- or t-butylthio, or represents phenyl, or—if m represents 2,—optionally also together with a second radical $R^3$ represents oxygen, propane-1,3-diyl or butane-1,4-diyl, $R^4$ represents hydroxyl, formyloxy, fluorine or chlorine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy,methylsulphonyloxy, ethylsulphonyloxy, n- or i-propylsulphonyloxy, represents in each case optionally fluorine-, chlorine- and/or bromine-substituted propenyloxy, butenyloxy, propinyloxy or butinyloxy, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenyloxy, phenylthio, phenylsulphinyl, phenylsulphonyl, phenylcarbonyloxy, phenylcarbonylalkoxy, phenylsulphonyloxy, phenylmethoxy, phenylmethylthio, phenylmethylsulphinyl or phenylmethylsulphonyl, $R^5$ represents hydrogen, cyano, carbamoyl, thiocarbamoyl, fluorine, chlorine or bromine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, or represents in each case optionally cyano-, fluorine-, chlorine-, methyl- or ethyl-substituted cyclopropyl, cyclobutyl, cyclopentyl or cyclohexyl, $R^6$ represents hydrogen, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally cyano-, fluorine-, chlorine- or bromine-substituted propenyl, butenyl, propinyl or butinyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, n-, i-, s- or t-butylthio-, difluoromethylthio-, trifluoromethylthio-, methylsulphinyl-, ethylsulphinyl-, trifluoromethylsulphinyl-, methylsulphonyl, ethylsulphonyl- or trifluoromethylsulphonyl-substituted phenyl or phenylmethyl, $R^7$ represents hydroxyl, formyloxy, represents in each case optionally cyano-, fluorine-, chlorine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, or represents in each case optionally cyano-, fluorine-, chlorine- or bromine-substituted propenyloxy, butenyloxy, propinyloxy or butinyloxy, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenylmethoxy, phenylcarbonyloxy, phenylcarbonylmethoxy or phenylsulphonyloxy, $R^8$ represents hydrogen, cyano, carbamoyl, thiocarbamoyl, fluorine, chlorine or bromine, or represents in each case optionally cyano-, fluorine-, chlorine-, methoxy-, ethoxy-, n- or i-propoxy-substituted methyl, ethyl, n- or i-propyl, n-, i-, s- or t-butyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl, $R^9$ represents hydrogen, represents in each case optionally cyano-, fluorine-, chlorine-, methoxy-, ethoxy-, n- or i-propoxy-substituted methyl, ethyl, n- or i-propyl, n-, i-, s- or t-butyl, or represents in each case optionally cyano-, fluorine-, chlorine-, methyl- or ethyl-substituted cyclopropyl, cyclobutyl, cyclopentyl or cyclohexyl, $R^{10}$ represents hydrogen, represents in each case optionally cyano-, fluorine-, chlorine-, methoxy-, ethoxy-, n- or i-propoxy-substituted methyl, ethyl, n- or i-propyl, n-, i-, s- or t-butyl, or represents in each case optionally cyano-, fluorine-, chlorine-, methyl- or ethyl-substituted cyclopropyl, cyclobutyl, cyclopentyl or cyclohexyl, and $R^{11}$ represents hydrogen, cyano, carbamoyl, fluorine, chlorine or bromine or represents in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl with the proviso that when Q is oxygen, $R^2$ is not cyclopropyl and Z is not

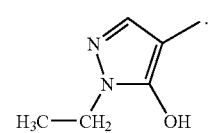

4. A compound of the Formula (I) according to claim 1, wherein $A^2$ represents methylene (—CH$_2$—), ethane-1,2-diyl (dimethylene, —CH$_2$CH$_2$—) or propane-1,3-diyl (—CH$_2$CH$_2$CH$_2$—), $R^1$ represents hydrogen, represents in each case optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n- or i-butyl, represents methoxy, ethoxy, n- or i-propoxy, methylthio, ethylthio, n- or i-propylthio, methylamino, ethylamino, n- or i-propylamino, represents dimethylamino, represents in each case optionally fluorine- and/or chlorine-substituted propenyl, butenyl, ethinyl, propinyl or butinyl, represents in each case optionally cyano-, fluorine-, chlorine- or methyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, phenylmethyl or phenylethyl, or represents the grouping —C(Q)-R$^2$, $R^2$ represents hydrogen, amino, hydroxyamino, hydrazino, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, methylthio, ethylthio, n- or i-propylthio, methylamino, ethylamino, n- or i-propylamino, methoxyamino, ethoxyamino, n- or i-propoxyamino, represents dimethylamino, represents N-methyl-methoxyamino, represents dimethylhydrazino, represents in each case optionally fluorine- and/or chlorine-substituted ethenyl, propenyl, butenyl, propenyloxy, butenyloxy, propenylthio, butenylthio, propenylamino, butenylamino, ethinyl, propinyl, butinyl, propinyloxy, butinyloxy, propinylamino or butinylamino, represents in each case optionally cyano-, fluorine-, chlorine- or methyl-substituted cyclopropyl, cyclobutyl, cyclopentyl, cyclohexyl, cyclopropylmethyl, cyclobutylmethyl, cyclopentylmethyl or cyclohexylmethyl, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, phenylamino, phenylmethyl or phenylethyl, or represents in each case optionally nitro-, cyano-, fluorine-, chlorine-, bromine-, methyl-, ethyl-, n- or i-propyl-, n-, i-, s- or t-butyl-, difluoromethyl-, trifluoromethyl-, dichloromethyl-, trichloromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methoxycarbonyl-, ethoxycarbonyl-, n- or i-propoxycarbonyl-substituted monocyclic or bicyclic heterocyclyl or heterocyclylalkyl from the group consisting of furyl, furylmethyl, thienyl, thienylmethyl, pyrrolidinyl, oxopyrrolidinyl, pyrrolyl, pyrrolylmethyl, pyrazolyl, pyrazolylmethyl, imidazolyl, imidazolylmethyl, 2-oxo-1,3-diazacyclopentyl, oxazolyl, isoxazolyl, oxazolylmethyl, isoxazolidinyl, thiazolyl, thiazolylmethyl, piperidinyl, oxopiperidinyl, 2-oxo-1,3-diazacyclohexyl, morpholinyl, piperazinyl, pyridinyl, pyridinylmethyl, pyrimidinyl, pyrimidinylmethyl, X represents hydrogen, nitro, cyano, fluorine, chlorine, bromine, iodine, methyl, ethyl, n- or i-propyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl, Y represents hydrogen, nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl, m represents the number 0 or 1, $R^3$ represents hydrogen, represents in each case optionally fluorine- and/or chlorine-substituted methyl, ethyl, n- or i-propyl, methylthio, ethylthio, n- or i-propylthio, or represents phenyl, or—if m represents 2—optionally also together with a second radical $R^3$ represents oxygen, propane-1,3-diyl or butane-1,4-diyl, $R^4$ represents hydroxyl, represents formyloxy, represents in each case optionally fluorine- and/or chlorine-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine- and/or chlorine-substituted propenyloxy, butenyloxy, propinyloxy or butinyloxy, represents in each case optionally nitro-, cyano-, fluorine-, chlorine-, bromine- methyl-, ethyl-, n- or i-propyl-, trifluoromethyl-, methoxy-, ethoxy-, n- or i-propoxy-, difluoromethoxy- or trifluoromethoxy-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl or phenylmethylsulphonyl, $R^5$ represents hydrogen, cyano, fluorine, chlorine, represents in each case optionally fluorine- and/or chlorine-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, or represents in each case optionally cyano-, fluorine-, chlorine- or methyl-substituted cyclopropyl, $R^6$ represents hydrogen, represents in each case optionally cyano-, fluorine-, chlorine-, methoxy or ethoxy-substituted methyl, ethyl, n- or i-propyl, n-, i-, s- or t-butyl, represents in each case optionally fluorine- or chlorine-substituted propenyl, butenyl, propinyl or butinyl, represents in each case optionally fluorine-, chlorine- or methyl-substituted cyclopropyl, cyclobutyl, cyclopentyl or cyclohexyl, or represents in each case optionally fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenyl or phenylmethyl, $R^7$ represents hydroxyl, represents formyloxy, represents in each case optionally cyano-, fluorine-, chlorine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine- and/or chlorine-substituted propenyloxy, butenyloxy, propinyloxy or butinyloxy, or represents in each case optionally nitro-, cyano-, fluorine-, chlorine-, bromine-, methyl-, ethyl-, n- or i-propyl-, trifluoromethyl-, methoxy-, ethoxy-, n- or i-propoxy, difluoromethoxy- or trifluoromethoxy-substituted phenylmethoxy, phenylcarbonyloxy, phenylcarbonylmethoxy or phenylsulphonyloxy, $R^8$ represents hydrogen, cyano, fluorine, chlorine, bromine, or represents in each case optionally fluorine-, chlorine-, methoxy- or ethoxy-substituted methyl, ethyl, n- or i-propyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl, $R^9$ represents hydrogen, represents in each case optionally fluorine-, chlorine-, methoxy- or ethoxy-substituted methyl, ethyl, n- or i-propyl, or represents optionally fluorine-, chlorine- or methyl-substituted cyclopropyl, $R^{10}$ represents hydrogen, represents optionally fluorine-, chlorine-, methoxy- or ethoxy-substituted methyl, ethyl, n- or i-propyl, or represents optionally fluorine-, chlorine- or methyl-substituted cyclopropyl, and $R^{11}$ represents hydrogen, cyano, fluorine, chlorine, bromine, or represents in each case optionally fluorine-, chlorine-, methoxy-, or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl with the proviso that when Q is oxygen, $R^2$ is not cyclopropyl and Z is not

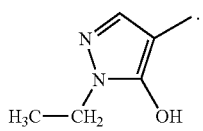

5. A compound of the Formula (I) according to claim 1, wherein $R^1$ represents hydrogen, or represents in each case optionally fluorine-, chlorine-, methoxy- or ethoxy-substituted methyl, ethyl, n- or i-propyl, represents methoxy or ethoxy or represents the grouping —C(Q)-$R^2$, $R^2$ represents hydrogen, amino, hydrazino, or represents in each case optionally fluorine-, chlorine-, methoxy- or ethoxy-substituted methyl, ethyl or n- or i-propyl, represents dimethylamino, represents in each case optionally fluorine-, chlorine- or methyl-substituted cyclopropyl, cyclobutyl, cyclopentyl or cyclohexyl, represents in each case optionally nitro-, cyano-, fluorine-, chlorine-, bromine- methyl-, ethyl-, n- or i-propyl-, methoxy-, ethoxy- or n- or i-propoxy-substituted phenyl, phenylamino, phenylmethyl or phenylethyl, or represents in each case optionally nitro-, cyano-, fluorine-, chlorine-, bromine-, methyl-, ethyl-, difluoromethyl-, trifluoromethyl-, dichloromethyl-, trichloromethyl-, chlorodifluoromethyl-, fluorodichloromethyl-, methoxy-, ethoxy-, methylthio-, ethylthio-, difluoromethylthio-, trifluoromethylthio-, methoxycarbonyl-, ethoxycarbonyl-substituted furyl, furylmethyl, thienyl, thienylmethyl, pyrrolyl or pyrrolylmethyl, X represents hydrogen, nitro, fluorine, chlorine, bromine, methyl, ethyl or trifluoromethyl, Y represents hydrogen, nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl, $R^3$ represents hydrogen or in each case optionally fluorine- and/or chlorine-substituted methyl or ethyl, $R^4$ represents hydroxyl, $R^5$ represents hydrogen, fluorine, chlorine or represents in each case optionally fluorine- and/or chlorine-substituted methyl, ethyl, methoxy or ethoxy, $R^6$ represents hydrogen or represents in each case optionally fluorine-, chlorine-, methoxy- or ethoxy-substituted methyl, ethyl, n- or i-propyl, n-, i-, s- or t-butyl, $R^7$ represents hydroxyl, or represents in each case optionally fluorine-, or chlorine-substituted methoxy or ethoxy, or represents optionally nitro-, cyano-, fluorine-, chlorine-, bromine, methyl-, ethyl-, trifluoromethyl-, methoxy- or ethoxy-substituted phenylmethoxy with the proviso that when Q is oxygen, $R^2$ is not cyclopropyl and Z is not

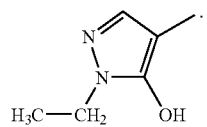

6. A process for preparing a compound of the Formula I according to claim 1, comprsing (a) reacting a compound of the Formula (II)

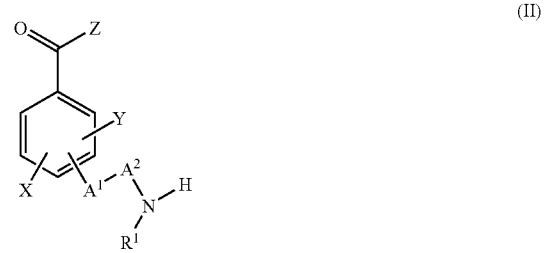

in which
A¹, A², R¹, X, Y and Z are as defined in claim 1,
with a compound of the Formula (III)

(III)

in which
Q and R² are as defined in claim 1 and
Q¹ represents halogen, alkoxy, alkylthio, aryloxy or arylthio,
—or, optionally, with corresponding iso(thio)cyanates—
optionally in the presence of one or more reaction auxiliaries and
optionally in the presence of one or more diluents,
or
(b) reacting a carboxylic acids of the Formula (IV)

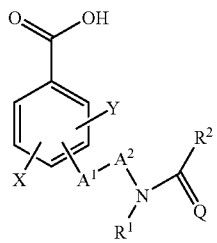
(IV)

in which
A¹, A², Q, R¹, R², X and Y are as defined in claim 1,
—or reactive derivatives thereof including corresponding acid halides, acid cyanides or esters—
with a compound of the Formula (V)

H-Z   (V)

in which
Z is as defined in claim 1,
optionally in the presence of a dehydrating agent and also,
optionally in the presence of one or more reaction auxiliaries and,
optionally, in the presence of one or more diluents,
or
(c) reacting a substituted benzoyl ketones of the Formula (Ia)

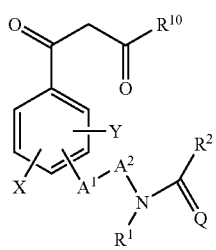
(Ia)

in which
A¹, A², Q, R¹, R², R¹⁰, X and Y are as defined in claim 1,
with an orthoformic ester or with a N,N-dimethyl-formamide acetal or with a cyanoformic ester or with carbon disulphide and an alkylating agent and subsequently with hydroxylamine or an acid adduct thereof,
optionally in the presence of one or more reaction auxiliaries and
optionally in the presence of one or more diluents,
or
(d) reacting an aryl ketone of the Formula (VI)

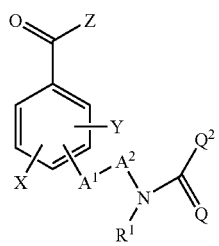
(VI)

in which
A¹, A², Q, R¹, X, Y and Z are as defined in claim 1 and
Q² represents halogen, alkoxy, alkylthio, aryloxy or arylthio,
—or, optionally, corresponding iso(thio)cyanates—
with a compound of the Formula (VII)

H—R²   (VII)

in which
R² is as defined in claim 1,
optionally in the presence of one or more reaction auxiliaries and
optionally in the presence of one or more diluents,
and wherein optionally, the resulting compound of the Formula (I) of the respective processes (a), (b), (c) or (d), are subjected to subsequent reactions for conversion into other compounds within the definition of the Formula (I).

7. A herbicidal composition comprising at least one compound according to any one of claims 1 to 5 and an extender.

8. A method for controlling undesirable plants, comprising allowing at least one compound according to any one of claims 1 to 5 or a composition according to claim 7 to act on the undesirable plants and/or their habitat.

\* \* \* \* \*